United States Patent [19]

Margel et al.

[11] Patent Number: 5,855,987
[45] Date of Patent: Jan. 5, 1999

[54] BIOACTIVE CONJUGATES OF CELLULOSE WITH AMINO COMPOUNDS

[75] Inventors: Shlomo Margel, Rehovot; Sophia Sturchak, Tel Aviv, both of Israel

[73] Assignee: Bar Ilan University, Ramat Gan, Israel

[21] Appl. No.: 416,351

[22] Filed: Apr. 4, 1995

Related U.S. Application Data

[62] Division of Ser. No. 196,390, Feb. 10, 1994, Pat. No. 5,516,673.

[30] Foreign Application Priority Data

Feb. 15, 1993 [IL] Israel ......................................... 104734

[51] Int. Cl.$^6$ ............................... B32B 3/00; B32B 27/14
[52] U.S. Cl. ......................... 428/195; 428/206; 435/188; 514/2; 514/410; 523/111; 524/18; 524/35; 524/503; 525/54.1; 527/54.1
[58] Field of Search ..................................... 428/195, 206; 435/188; 523/111; 524/18, 35, 503; 525/54.1; 527/103; 530/8.5; 514/2, 410; 536/56, 72, 75

[56] References Cited

U.S. PATENT DOCUMENTS

| | | | |
|---|---|---|---|
| 4,617,326 | 10/1986 | Bjornberg et al. | 523/111 |
| 5,008,385 | 4/1991 | Diamantoglou | 536/56 |
| 5,019,500 | 5/1991 | Veda et al. | 530/351 |
| 5,028,531 | 7/1991 | Veda et al. | 536/27 |
| 5,053,423 | 10/1991 | Liu | 514/410 |
| 5,238,940 | 8/1993 | Liu et al. | 514/410 |
| 5,330,823 | 7/1994 | Malhotra | 428/195 |

FOREIGN PATENT DOCUMENTS

| | | |
|---|---|---|
| 117365 | 11/1981 | U.S.S.R. . |
| 210938 | 11/1984 | U.S.S.R. . |
| 2147206 | 5/1985 | United Kingdom . |

OTHER PUBLICATIONS

L. Peng et al. *Applied Biochem. and Biotech.* 14, 91 1987.
C. Flemming et al. *Acta Biol.Med.Ger.* 31, 449 (1973).
K. Schwertassek et al. *Textiltechn.* 9, 361 (1956).
S.C. Davis et al. *J.Surg.Res.* 48, 245 (1990).
M. Singh et al. *J. of Biobeam. Mat. Res.* 15, 655 (1981).
S. Margel et al. *J. Polym.Sci. Chem.* Ed. 22, 145 1984.
S. Margel *J. of Chromatography*, 462, 177 (1989).
E. V. Groman et al. *Tibtech,* 5, 220 (1987).
K. Nilsson et al. *Eur. J. Biochem,.* 112, 397 (1980).
A.R. Comfort et al. *Biotech and Bioeng.* 34, 1366 (1989).
Krantz and Carr, "Pharmacological Principles of Medical Practice", Eighth Edition, 1972, pp. 1001–1003.
Goodman and Gilman, "Pharmacological Basis of Therapeutics" 6th Ed., Macmillan Pub.Co., Ing., 1980, pp. 964–987.
L. Segal, *Cellulose and Cellulose Derivatives,* Part V (1970) Ed. N.M. Bikates and L. Segal, pp. 719–729.
Lowry et al. *J. Biol.Chem.* 193, 265.
K. Walsh et al. "Methods in Enzymology" 19, 31–41 (1970).
P.M. Gallop et al. *JBC,* 227 891 (1957).
D.F. Ollis and R. Datta, "Methods in Enzymology" 44, 444–450 (1976).
A. Linker, "Methods of Enzymatic Analysis" vol. 4, 256–262 (1984).
P.H. Berk et al. *J. Clin. Invest.,* 53. 778–785.
J.S. Paterson "The UFAW Handbook on Care and Management of Laboratory Animals" Ed. by UFAW, 223–241 (1972).
Colowick et al. (1976) *Methods in Enzymology,* vol. XLIV, pp. 444–450.

*Primary Examiner*—Helen Lee
*Attorney, Agent, or Firm*—Darby & Darby

[57] ABSTRACT

Polymers containing a plurality of free hydroxy groups, such as cellulose, agarose or polyvinyl alcohol, are contacted in absence of reactants for hydroxy groups, with at least one N-heterocyclic compound, e.g. pyridine, pyrrole, pyridazine, their partially or fully hydrogenated analogs and any of these which may be substituted, in a pre-activation step prior to reaction with reactant for free hydroxy groups in the polymer, the polymer-bound residue of which reactant may be thereafter reacted in turn with amino compounds containing at least one unsubstituted N-attached hydrogen atom, e.g. proteins, thereby to form amine-polymer conjugates. The invention further relates to a powder, bandage, patch or like cover for application to wounds which has been manufactured from polymer containing a plurality of hydroxy groups by a process which includes the step of providing an amine conjugated to the polymer; the amine may be, e.g., trypsin, chymotrypsin, lysozyme, collagenase, albumin and hyaluronidase.

4 Claims, 17 Drawing Sheets
(2 of 17 Drawing Sheet(s) filed in Color)

day 0 day 1 day 3 day 5

Trypsin coupled to dialdehyde cellulose (DALCEKS-TRYPSIN)

Trypsin coupled to cellulose by the new method

1

BIOACTIVE CONJUGATES OF CELLULOSE WITH AMINO COMPOUNDS

This is a division of application Ser. No. 08/196,390, filed Feb. 10, 1994, now U.S. Pat. No. 5,516,673.

BACKGROUND OF THE INVENTION

Reaction of amines with functionalized polymers

Covalent coupling of amines, which may be bioactive compounds, e.g. proteins, onto functionalized polymeric surfaces, is commonly accomplished by interacting amine groups of the proteins with desired functional groups of the polymers.

In particular, the binding of amino ligands, e.g. proteins, to polymers containing aldehyde groups (polyaldehyde polymers) is depicted in FIG. 1. The Schiff base products are unstable in aqueous solution since they are in equilibrium with the interacting reagents, but they may be stabilized, e.g. by reduction of the Schiff base bonds with an appropriate reducing agent, e.g. NaBH4.

Dialdehyde dextran and dialdehyde cellulose are examples of polyaldehyde polymers commonly used for immobilization of proteins through the formation of Schiff base products. These polymers are commonly obtained by periodate oxidation of vicinal hydroxyl groups of the parent polymers, dextran and cellulose, respectively, see J. Turkova, et al, Can. Pat. 1217134 (1987). The aldehyde content of these polymers can be controlled by oxidation conditions, i.e. periodate concentration. The backbone of these dialdehyde polymers has a completely different structure than that of the parent polymers (FIG. 2 ). This difference results in a more open structure, higher porosity, increased water solubility, increased biodegradability and decreased mechanical strength of the dialdehyde polymers relative to its parent polymers. For example, cellulose is considered to be a non-biodegradable polymer while dialdehyde cellulose is a biodegradable polymer, a property which is desired for controlled release studies (see M. Singh, P. Vasudevan, T. J. M. Sinha, A. R. Ray, M. M. Misro and K. Guha, J. of Biomed. Mat. Res. 15, 655 (1981)), but undesired for other biomedical applications, e.g. wounds treatment.

The Schiff base bonds formed by the interaction of dialdehyde polymers with proteins are not stable in aqueous solution (FIGS. 1 and 2), resulting in a leakage of the bound protein. Furthermore, the reaction of proteins with polyaldehyde polymers is usually incomplete, approximately 0.5%–10% of free aldehyde groups participating, see S. Margel and E. Wiesel, J. Polym. Sci., Chem. Ed. 22, 145 (1984). Therefore, residual aldehyde may intramolecularly interact with amino groups of the bound protein, thus significantly decreasing its activity, see S. Margel, J. of Chromatography, 462, 177 (1989). Blocking of residual aldehyde groups and stabilization of Schiff base bonds may be effected by reduction with reducing agents, e.g. NaBH4 (FIGS. 1 and 2). However, the reduced polymers possess significantly decreased mechanical strength, higher water solubility and frequently significantly decreased protein activity, due to reduction of bonds such as disulfide required for native protein activity, see L. Peng, G. J. Calton and J. B. Burnett, Applied Biochem. and Biotechn. 14, 91 (1987).

FIG. 3 describes the binding chemistry of proteins to polymers containing free hydroxy groups, e.g. cellulose, agarose, dextran, etc. This binding method is based on the activation of hydroxyl groups of the polymeric matrix by reaction with various reagents, e.g. cyanogen bromide, tosyl chloride, tresyl chloride, etc., see E. V. Groman, and M. Wilchek, TIBTECH, 5, 220 (1987). The activated polymer is then used for covalent binding of amino ligands (and thiol ligands), e.g. proteins, by nucleophilc-substitution reaction, according to FIG. 3.

The binding of amino (or thiol) ligands to polymers containing hydroxyl groups according to such a derivatization method has been intensively investigated, see K. Nilsson, K. Mosbach, Eur.J.Biochem., 112, 397 (1980). Generally, this reaction is accomplished by adding the dried polymer to an organic solvent (e.g. acetone or dioxane) containing a desired concentration of activating reagent (e.g. tosyl chloride, tresyl chloride, etc). A base (e.g. pyridine, triethylamine, etc) is then added to the organic solution in order to neutralize liberated HCl. The polymer is then washed with an appropriate organic solvent from an unbound activating reagent. The dried activated polymer is then reacted in aqueous solution with the desired amino (or thiol) ligand. Any unbound ligand may then be removed. If necessary, residual tosylate groups may be blocked by known methods, e.g. basic conditions or a reaction with a second amino (or thiol) ligand. The common organic bases used for neutralizing liberated HCl in this activation procedure are pyridine and triethylamine. A. R. Comfort, E. C. Albert and R. Langer, Biotech. and Bioeng. 34, 1366 (1989), demonstrated that the retention activity of heparinase bound to cellulose by tresyl chloride activation increased by threefold if triethylamine was used as organic base instead of pyridine.

The reaction of primary hydroxyl groups with p-toluene sulfonyl chloride (tosyl chloride) and/or trifluoroethane sulfonyl chloride (tresyl chloride) forms tosylate esters, which have excellent reactivity with amino (and thiol) ligands, as illustrated in FIG. 4. The structure of the cellulose backbone does not change during this immobilization method (FIG. 5), thereby its basic chemical and physical properties, i.e. solubility, mechanical properties, non-biodegradability, etc, remain almost unchanged. Furthermore, the chemical bonds formed by the above activation reagents, e.g. tosyl chloride and tresyl chloride, are stable, thus preventing any significant leakage of bound protein into the solvent, see S. P. Colowick and N. O. Kaplan in "Methods in Enzymology" 135-B, 29 (1987).

The treatment of wounds

Wounds may be defined as damage to the skin. A wound may be caused by a scratch on the skin, heat, cold, chemical substances (including radioactive substances), electricity, etc. The term wound also includes burns and scars. The skin is one of the most important sensory organ in the body and it is our defensive mechanism against the environment. When part of the skin is damaged, water, salts, proteins and energy are leaked out of the body through the damaged skin. The body loses a significant amount of heat, and bacteria may penetrate into the body through the damaged skin. Fungi and bacteria may cause local contamination in the wound with the threat of deep penetration into the body, resulting in total inflammation.

The purpose of treating wounds is to repair the damage caused to the skin. If the damage is small and local, it will usually take a few days or weeks to cure. However, if the damaged area is extensive and severe, the curing process will be slow and usually skin implantation and other treatments, e.g. drug administration, are essential. Often, curing wounds involves severe pains, leaves scars and requires physiotherapy and/or psychological treatment; in severe cases the treatment will have to deal with problems such as bleeding, contamination, pains, poisons, water accumulation, etc.

There are many methods currently in use for treatment of wounds, e.g. antiseptic and antibiotic preparations, laser illumination, cryotechniques, native enzyme preparations, etc., see e.g. Krantz and Carr in "Pharmacological Principles of Medical Practice", Eighth Edition, 1972, pp 1001–1003 "Agents for Treatment of Burns and Ulcers"; Goodman and Gilman in "Pharmacological Basis of Therapeutics", Sixth Ed., Macmillan Pub. Co., Inc., 1980, pp 964–987. Each method of treatment has both its advantages and disadvantages.

Among these methods, the use of native enzymes to treat wounds is quite common. These enzymatic preparations are generally based on enzymes such as proteolytic enzymes (e.g. trypsin and chymotrypsin), which cleanse purulent-necrotic wounds and reduce amount of pathogens), lysozyme (which dissolves bacteria cell walls), and/or collagenase (which decomposes collagen and prevents formation of rough scars). Enzymatic preparations usually take the form of gels, powders or liquids, which are spread on the wounds. The use of native proteolytic enzymes to treat wounds is quite common. However, this method suffers from some major shortcomings, e.g., native enzymes are rapidly inactivated by inhibitors, they are unstable in aqueous solutions, exhibit antigen and pyrogen properties, may penetrate into blood circulation and develop thereby an allergic reaction, and moreover they are expensive.

In order to overcome these disadvantages, some researchers have covalently coupled various proteolytic enzymes onto polymeric beads, of approximately 0.05–0.5 mm average diameter, composed of dextran dialdehyde and/or dialdehyde cellulose, see J. Turkova et al, Can. Pat. 1217134 (1987); C. Flemming, A. Gabert, P. Roth and H. Wand Acta Biol. Med. Ger. 31, 449 (1973). However, the use of these conjugated beads for treating wounds is limited because of a number of disadvantages, e.g. this method is relatively expensive, and the liquid frequently flows from the wounds and sweeps away the conjugated beads, making it necessary to repeat this treatment several times. Further major shortcomings of these dialdehyde polymers for wounds treatment have been mentioned above.

A novel method to treat wounds has recently been developed by Soviet scientists. This method is based on covalent binding of bioactive reagents, e.g. proteolytic enzymes, onto dialdehyde cellulose dressings and/or aldehyde-polycaproamide dressings. Dialdehyde cellulose dressings were formed by periodate oxidation of cellulose and aldehyde-polycaproamide dressings were formed by acidic hydrolysis (3M HCl) of polycaproamide, followed by glutaraldehyde coupling to the terminal amino groups of the hydrolyzed products, see FIG. 6. Immobilized enzyme dressings, under the commercial name "PAKS-TRYPSIN" (trypsin bound onto aldehyde-polycaproamide, see K. Lakin, V. Pronin, V. Ryltsev, S. Sturchak and V. Filatov , USSR Pat. N 117365 (1981)) and "DALCEKS-TRYPSIN" (trypsin bound onto dialdehyde cellulose, see S. Sturchak, V. Filatov, K. Lakin and V. Ryltsev, USSR Pat. N 210938 (1984)), are commercially available. These immobilized dressings solved the problem of the previous polyaldehyde beads, whereby liquid flowing from the wounds frequently sweeps away the conjugated beads. However, other major shortcomings of polyaldehyde polymers, i.e. unstable bonds, leakage of bound enzymes into the body liquid, poor mechanical properties, water solubility, biodegradability, etc., still existed.

The entire disclosures of the literature and patent references mentioned herein are explicitly incorporated by reference in the present specification.

SUMMARY OF THE INVENTION

The present invention provides in one aspect a method for preactivating polymers containing a plurality of free hydroxy groups. The presently preferred polymers are polysaccharides, but it is to be understood that reference herein to polysaccharides is exemplary, and that the invention accordingly applies to other hydroxy-polymers such as, e.g., polyvinyl alcohol and its copolymers, e.g. with polyolefins such as polyethylene, as well as grafted polymers based on polyolefins such as polyethylene and which contain surface hydroxyl groups. The method according to the invention comprises contacting the hydroxy-polymer in absence of reactants for hydroxy groups, with at least one N-heterocyclic compound, e.g. pyridine (substituted and unsubstituted); pyrrole (substituted and unsubstituted); or pyridazine (substituted and unsubstituted). The N-heterocyclic ring in such compounds may be partially or fully saturated, as e.g., in the case of pyrroline, pyrrolidine or piperidine, and these compounds may be substituted or unsubstituted. When the N-heterocyclic compound is substituted, it preferably contains at least one substituent selected from $C_{1-6}$ alkyl, $C_{1-6}$ alkoxy, fluorine, chlorine, bromine and trifluoromethyl. The polymers thus preactivated also form part of the invention.

In another aspect, the invention provides a method for making a derivatized polysaccharide polymer, which comprises making a preactivated polymer as just described, and then reacting it with at least one reactant for free hydroxy groups in said polymer, said reactant being such that it contains, at least potentially, at least one functional group capable of reacting with amino groups containing unsubstituted hydrogen atoms, and being preferably selected from cyanogen halides, carbonate esters, halogenated s-triazines, haloformates, sulfonyl halides and N-heterocyclic compounds containing nuclear-bound active halogen atoms.

In a process for making conjugates of at least one amino compound containing at least one unsubstituted N-attached hydrogen atom with at least one polysaccharide polymer containing a plurality of free hydroxy groups, comprising at least steps (a) and (b) of the following steps (a), (b) and (c), namely: (a) derivatizing the at least one polysaccharide polymer by reaction with at least one reactant for free hydroxy groups in said polymer, such reactant being additionally characterized by the fact that it contains, at least potentially, at least one functional group capable of reacting with said at least one amino compound, (b) reacting the thus-derivatized polysaccharide polymer with the at least one amino compound, and optionally (c) reconverting to hydroxy groups by known methods any polymer-bound groups which are the product of reacting polysaccharide hydroxy groups with such reactant; the present invention in particular provides the improvement which comprises effecting a preactivation step prior to step (a) in order to increase the capacity of the at least one polysaccharide polymer for reaction with such at least one reactant, wherein said preactivation step consists of contacting said at least one polysaccharide polymer in absence of reactants for hydroxy groups, with at least one N-heterocyclic compound. The at least one amino compound may comprise at least one protein, e.g. trypsin, chymotrypsin, lysozyme, collagenase, albumin and/or hyaluronidase.

The at least one polysaccharide polymer (which is preferably cellulose but is not limited thereto), both prior to said process and at the end of said process, may be e.g. in powdered form, or in the form of a textile web which may be adapted for use as a bandage, patch or like wound cover.

The invention further relates to a powder, bandage, patch or like cover for application to wounds which has been manufactured from polymer containing a plurality of hydroxy groups by a process which includes the step of providing an amine, such as a protein, conjugated to the polymer. Without detracting from the generality of such wound cover containing amine conjugated to the polymer, such manufacturing process may include the method described herein for conjugating the amine to the polymer. Where the amine is a protein, this may be, e.g., one selected from trypsin, chymotrypsin, lysozyme, collagenase, albumin and hyaluronidase. The amine, in particular a protein (e.g. an enzyme), which has been conjugated to the polymer containing hydroxy groups following pretreatment of the polymer by contacting it in absence of reactants for hydroxy groups, with at least one N-heterocyclic compound, as described herein, has been found to have the important advantage that it has an -activity which is significantly greater than when such pretreatment has not been effected. The present invention yet further provides conjugates of at least one amino compound containing at least one unsubstituted N-attached hydrogen atom with at least one polymer containing a plurality of hydroxy groups, which have been obtained according to the process described herein.

The file of this patent contains at least one drawing executed in color. Copies of this patent with color drawings will be provided by the Patent and Trademark Office upon request and payment of the necessary fee.

DETAILED DESCRIPTION OF THE INVENTION

According to an embodiment of the present invention, bioactive compounds such as proteins may be conjugated with (and thus immobilized on) cellulose via its hydroxyl groups. Usually, increased activating agent binding capacity, similar or increased protein binding capacity, increased hygroscopicity and higher activity of the bound proteins were obtained by using this new activation method as compared to the known one.

Figure 1:
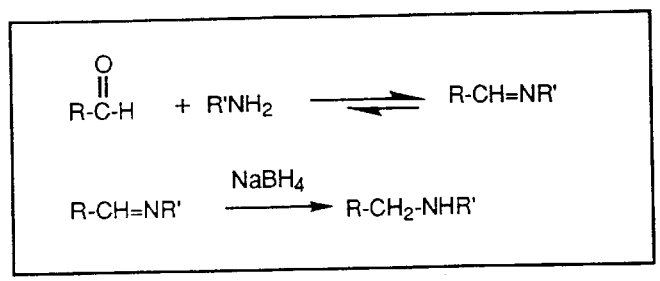
FIG. 1 depicts a scheme describing the coupling of amino ligands, e.g. proteins, to polymers containing aldehyde groups.
Figure 2:
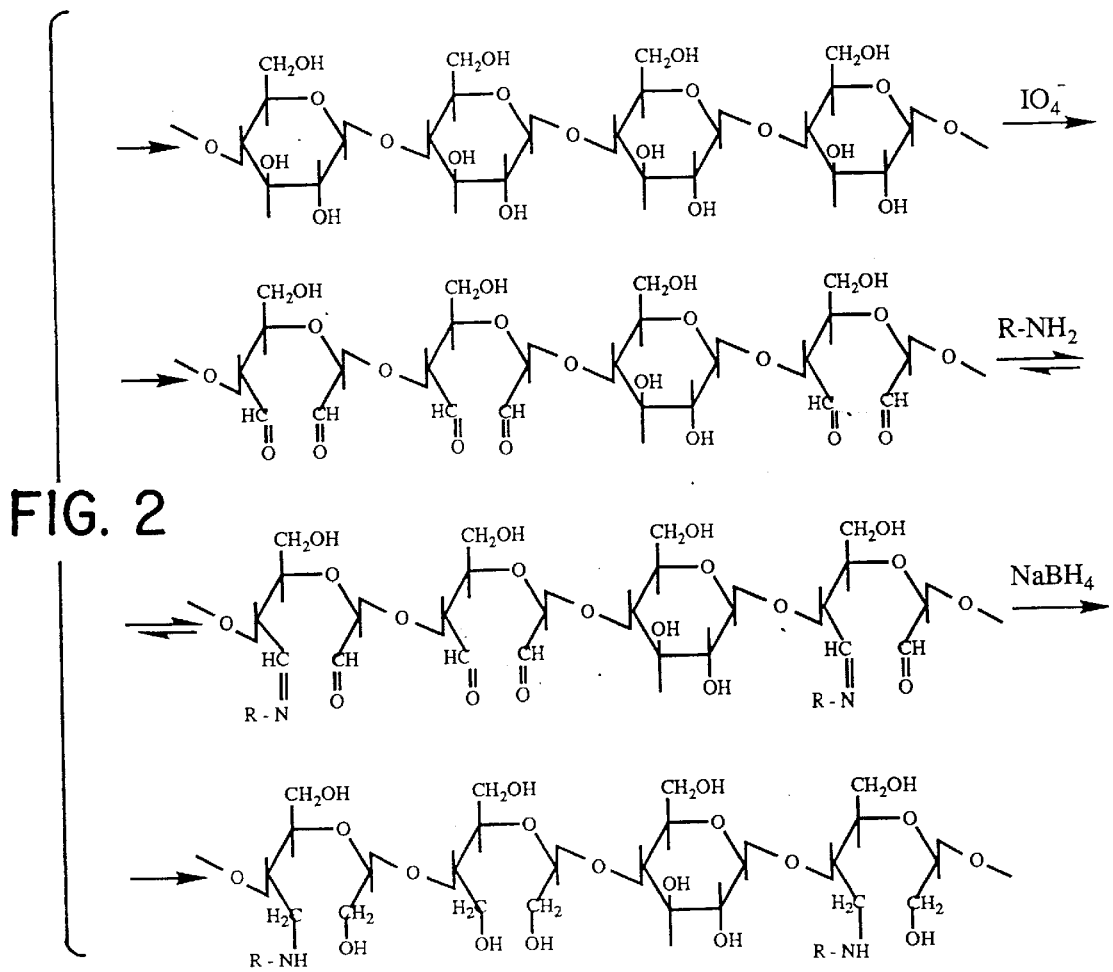
FIG. 2 depicts a scheme describing the periodate oxidation of cellulose and the coupling of amino ligands, e.g. proteins, to the resulted dialdehyde cellulose.
Figure 3:
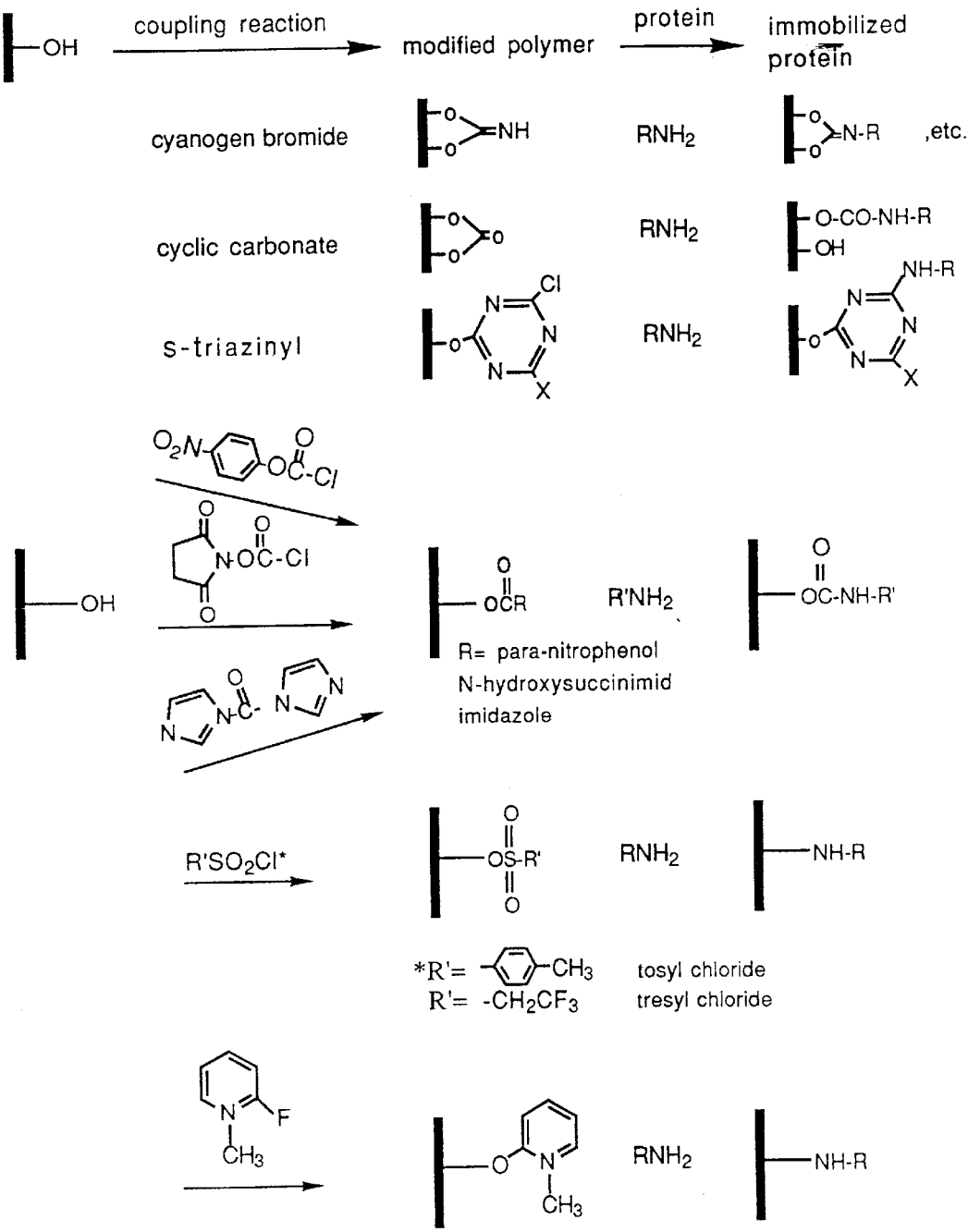
FIG. 3 depicts the activation of hydroxyl-containing polymers for covalent coupling of amino ligands, e.g. proteins.
Figure 4:
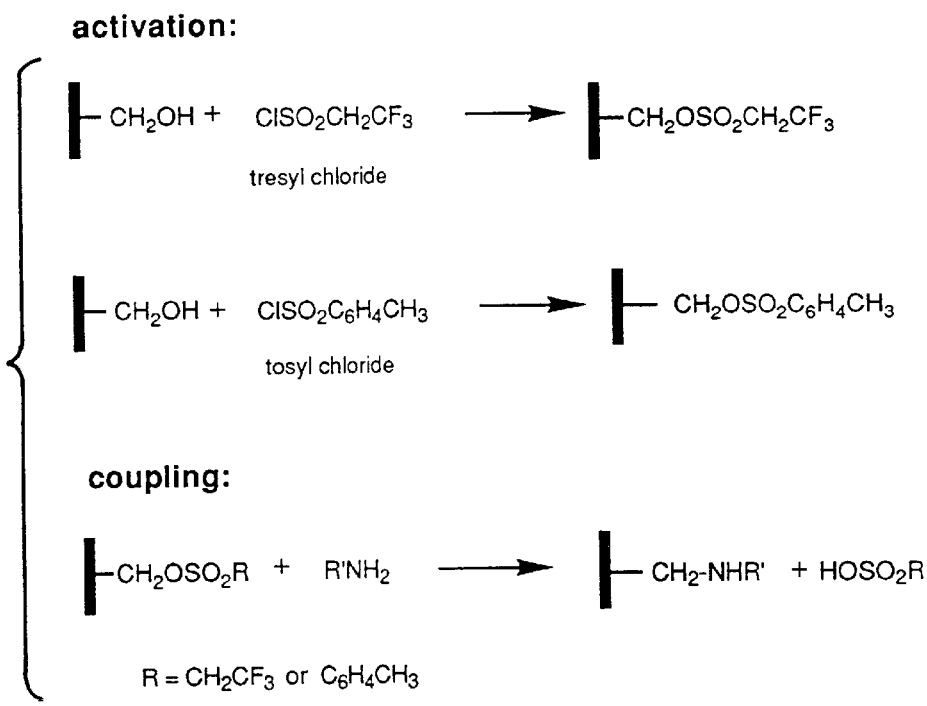
FIG. 4 depicts a scheme describing the binding of amino ligands e.g. proteins, to polymers containing hydroxyl groups, by means of tosyl chloride and tresyl chloride.
Figure 5:
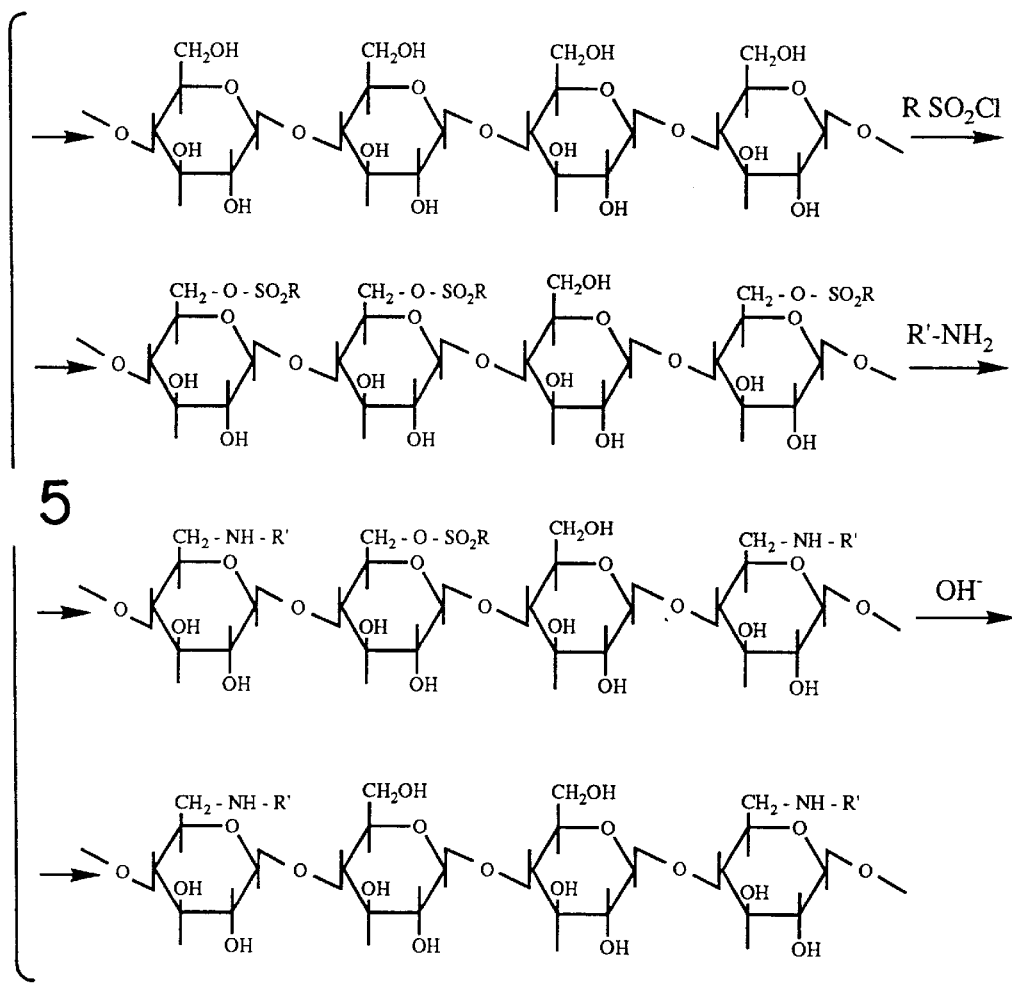
FIG. 5 depicts a scheme describing the interaction of cellulose with amino ligands, e.g. proteins, by means of tosyl chloride or tresyl chloride.
Figure 6:
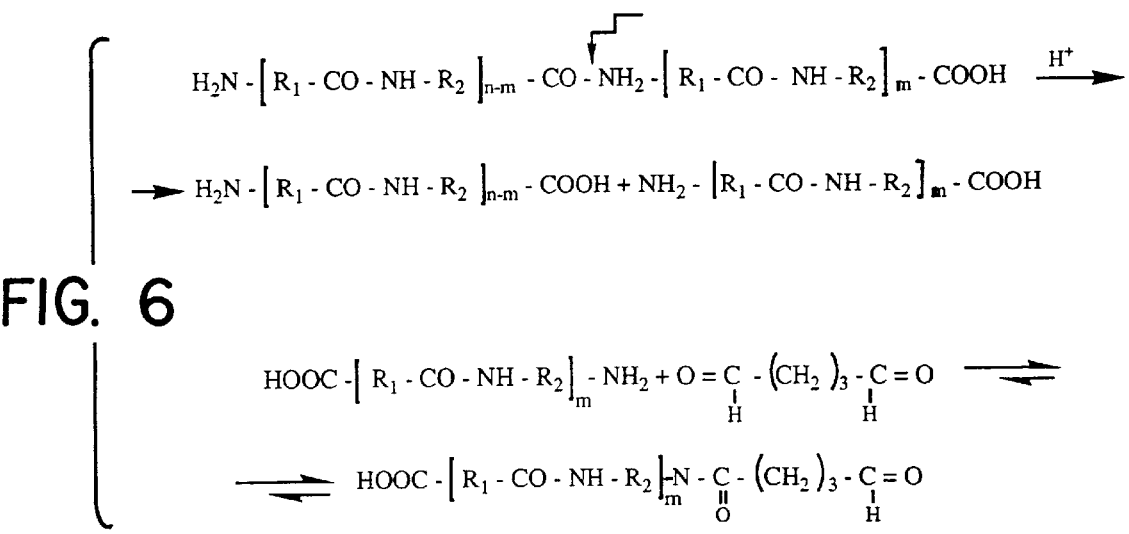
FIG. 6 depicts a scheme describing the hydrolysis of polycaproamide and the binding of glutaraldehyde to the hydrolyzed product.
Figure 7:
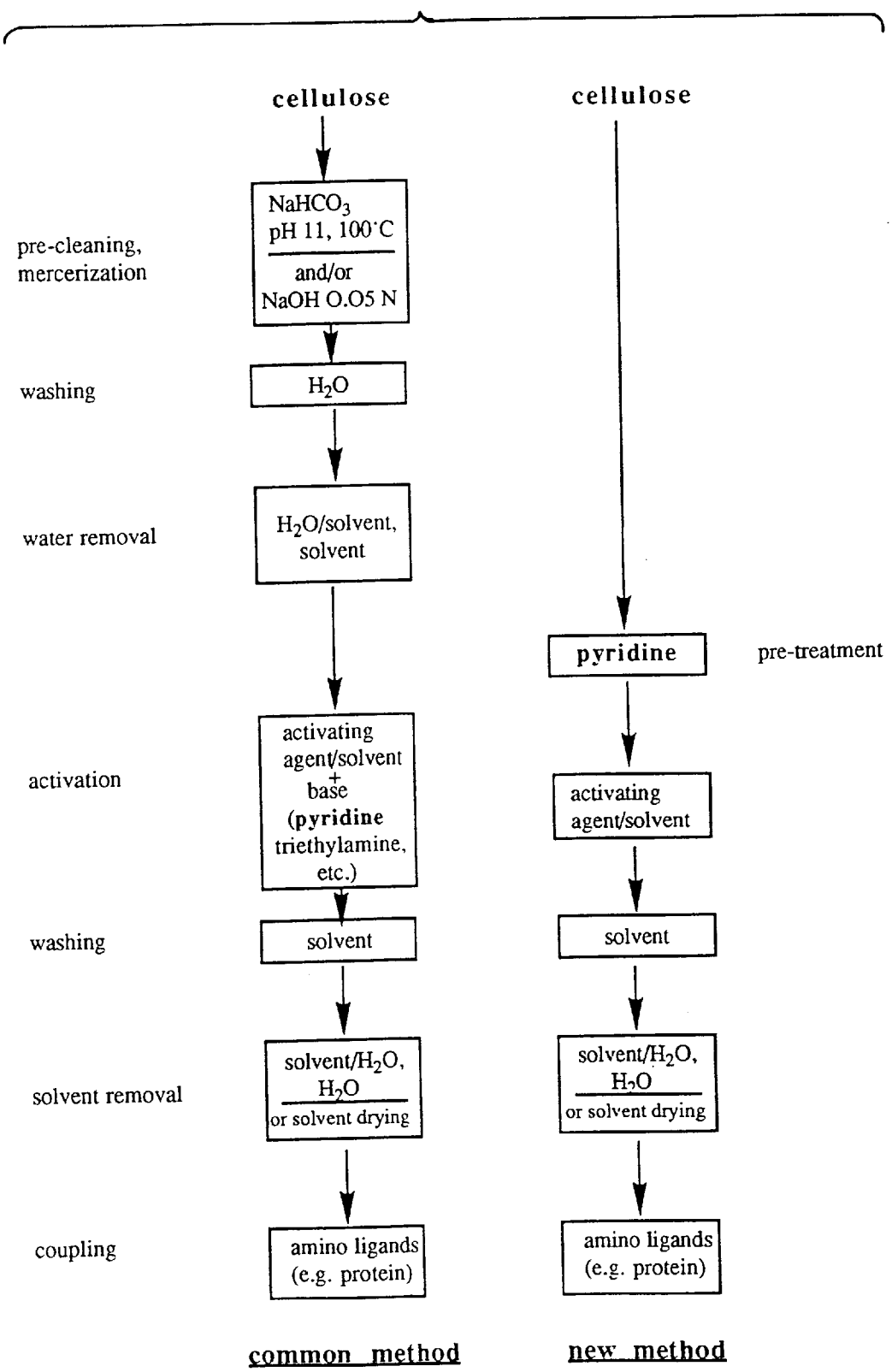
FIG. 7 depicts a scheme describing the known activation method and a method in accordance with an embodiment of the invention, for coupling amino ligands, e.g. proteins, to cellulose through its hydroxyl groups.

FIG. 7 demonstrates the major differences between the known activation method and the method in accordance with an embodiment of the invention. A major difference between this new activation method and the known one is due to the pre-treatment step, e.g. of cellulose with an N-heterocyclic base such as pyridine. It is believed that this pre-treatment breaks hydrogen bonds between cellulose chains, entrapping pyridine molecules between cellulose chains (c.f. L. Segal in "Cellulose and Cellulose Derivatives", Part V (1970) Ed. N.

Figure 8:
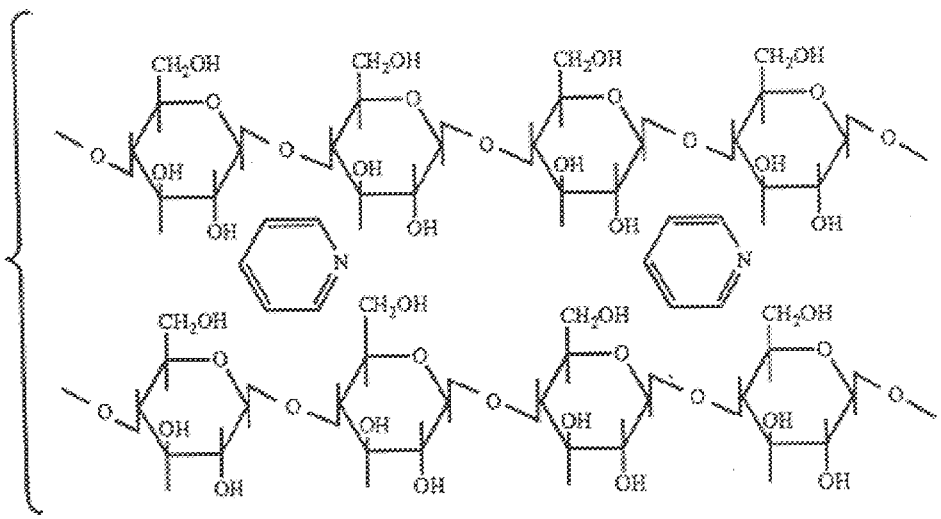
FIG. 8 depicts a scheme describing the inclusion of pyridine in cellulose.

M. Bikates and L. Segal, pp 719–729)) and results in a more open reactive form of cellulose (FIG. 8). Other differences between the new and known derivatization methods are due to the facts that in the new method, cellulose treatment by aqueous $NaHCO_3$ and/or NaOH (mercerization) is not essential and initial wet cellulose (approx. 6% $H_2O$) can also be used in the immobilization process.

Attempts to substitute other bases and/or swelling reagents, in the preactivation step, e.g. acetone, dioxane, dimethylsulfoxide, triethylamine, propylamine, etc, did not indicate any unusual behavior as compared with the invention.

The present invention also makes available novel polymeric surfaces composed of polysaccharides such as cellulose, coupled with proteins, such as trypsin, lysozyme, etc., for the treatment of wounds. These conjugated cellulose materials, in different manufactured forms, such as powders and dressings, are basically different from the commercial ones, e.g. PAKS-TRYPSIN and DALCEKS-TRYPSIN, because of the reasons previously described (different backbone structure, nonbiodegradability, higher mechanical strength, and stable bonds between the protein and the polymer). The conjugated materials obtained by the new activation method were significantly more efficient for wounds treatment than those obtained by the known method. For example, the activity of trypsin bound onto cellulose through the new activation method was approximately 5–10 times higher than that obtained by the known method as well as that obtained by DALCEKS-TRYPSIN and PAKS-TRYPSIN, although a similar amount of enzyme was bound to the polymers.

MATERIALS AND METHODS

The following materials were used in these studies: acetone, 1,4-dioxane, triethylamine and propylamine from BIO-LAB Laboratories Ltd., Israel; agarose, albumin (human fraction V), bilirubin (from bovine gall stones), pyridazine, pyrrole, pyrrolidine, pyrroline, piperidine, p-toluenesulfonyl chloride (tosyl chloride) and 2,2,2-trifluoro-ethanesulfonyl chloride (tresyl chloride) from Sigma, St. Louis, Mo.; pyridine, Folin-Ciocalteus phenolreagent, NaCl, $NaHCO_3$, NaOH, $KH_2PO_4$, $NaIO_4$, $NaBH_4$, Tris(hydroxymethyl)aminomethane, ethanolamine, mercapto-ethanol and activated molecular sieve 4A from Merck, Darmstadt, Germany. Cellulose (cotton)—medical gauze from Central Medical Supply A.R.M., Israel; cellulose powder MN 300 from Duren, Germany; trypsin from bovine pancreas-type III, collagenase- type XI, lysozyme from chicken egg white and hyaluronidase from bovine testes-type IV-S from Sigma, St. Louis Mo.; Na-benzoyl-1-arginine ethyl ester (BAEE) hydrochloride, collagen from bovine Achilles tendon-type I, insoluble, lyophilized cells of micrococcus lysodeikticus and hyaluronic acid from human umbilical cordsodium salt from Sigma, St. Louis, Mo.

Experimental animals: female guinea-pigs from Anilab., Rehovot, Israel, weighting 300–330 g were conditioned for two weeks prior to experiments. The animals received water and basal diet without antibiotics and were housed with controlled temperature (23°–25° C.) and light and dark (12 h/12 h LD).

METHODS OF ANALYSIS

A. The amounts of polymer-bound tosyl and/or tresyl groups were derived from the amount of sulfur determined by elemental analysis and from the absorption peaks of aqueous solution received after hydrolysis of the bound tosyl (and/or tresyl) groups (e.g. 261 nm, A261, for tosyl groups). Hydrolysis of these groups was accomplished by soaking the tosyl (and/or tresyl) activated cellulose (1 g) at room temperature for 1 h in 10 ml of NaHCO3 aqueous solution (0.05M) at pH 11.

B. The amounts of protein (enzyme) coupled to the polymers was measured by the method of Lowry et al., J.Biol.Chem., 193, 265 (1951).

C. Enzyme activity of coupled trypsin was measured according to K. A. Walsh and P. E. Wilcox, in "Methods in Enzymology" 19, 31–41 (1970) using BAEE as enzyme substrate. One BAEE unit activity produces an increasing in A253 of 0.001 per min. at pH 7.6 at 25° C., reaction volume 3.3 ml.

D. Enzyme activity of coupled collagenase was measured according to P. M. Gallop, S. Seifer and E. Meilman, JBC, 227, 891 (1957) using suspension of powdered "insoluble" collagen of bovine Achilles tendon as substrate. A unit activity of collagenase was defined as that amount causing dissolution of 1 mg of suspended collagen under the assay condition (37° C., incubation for 20 min. at pH 7.4).

E. Enzyme activity of coupled lysozyme was measured according to D. F. Ollis and R. Datta, in "Methods in Enzymology" 44, 444–450 (1976) using dried cells of micrococcus lysodeikticus as substrate. One unit activity of lysozyme is considered as the decrease in A450 of 0.001 per min. as a result of lysis of the corresponding substrate under experimental conditions (pH 7.0, 25° C., 0.3 mg/ml suspension of cells, reaction volume 3 ml).

F. Enzyme activity of coupled hyaluronidase was measured according to A. Linker, in "Methods of Enzymatic Analysis" vol.4, 256–262 (1984) using hyaluronic acid as substrate. One unit activity of hyaluronidase is expressed as fmol N-acetylglucosamine liberated per min. under the assay condition (37° C. at pH7.5, incubation volume 1 ml).

G. The activity of coupled albumin was measured according to Plotz, P. H., Berk, P., Scharschmidt, B. F., Gordon, J. K. and Vergalla, J., J. Clin. Invest. 53, 778–785 (1974), using bilirubin as substrate. Activity of albumin is expressed as % bilirubin absorbed from a model solution (0.005 mg/ml carbonate buffer, 0.1M, pH 8.5) onto cellulose at 25° C., incubation for 15 minutes with 25 mg cellulose, reaction volume 3 ml.

H. Hygroscopicity of the bioactive polymers was measured by the method of K. Schwertassek, J. Doubeck and U. Fasheforch, Textiltechn., 9, 361 (1956).

PRE-CLEANING OF POLYMERS

A. Pre-cleaning, mercerization, of cellulose.

1 g cellulose (cotton gauze and/or powder) was boiled for 30 min. in 25 ml of 1% NaHCO3 aqueous solution and/or 0.05N NaOH aqueous solution, the mixture cooled to room temperature, and the cellulose was washed extensively with distilled water, dried at room temperature and stored until used.

B. Pre-cleaning of polycaproamide (capron knitted cloth).

1 g polycaproamide was incubated at 60° C. for 30 min. in 15 ml 1% NaHCO3 aqueous solution. The solution was then cooled to room temperature, then the polycaproamide was washed extensively with distilled water, dried at room temperature and stored then until used.

Synthesis of trypsin-coupled polymers

A. Dialdehyde cellulose coupled with trypsin (DALCEKS-TRYPSIN).

DALCEKS-TRYPSIN was prepared according to USSR Pat. N 210938 (1984) by S. Sturchak, V. Filatov, K. Lakin and V. Ryltsev. Briefly, dialdehyde cellulose was prepared by soaking at room temperature 1 g cellulose in 5 ml of 0.6M aqueous $NaIO_4$ at pH 5.0 for 24 h. The thus-oxidized cellulose was then washed extensively with distilled water until the absorption peak at 205 nm completely disappeared. The formed dialdehyde cellulose was then placed for 18 h at room temperature in 2.5 ml of K/Na phosphate buffer, pH 7.5, containing 0.1% (w/v) trypsin. The dialdehyde cellulose-trypsin conjugate was then washed with 50 ml of the same buffer and then with 5×50 ml of saline solution (0.85% aqueous NaCl solution). The washed dialdehyde cellulosetrypsin conjugate (DALCEKS-TRYPSIN) was then dried at room temperature and stored until used. In these studies, home-made DALCEKS-TRYPSIN and the commercial product gave similar results.

B. Polycaproamide coupled with trypsin (PAKS-TRYPSIN).

PAKS-TRYPSIN was prepared according to USSR Pat. N 117365 (1981) by K. Lakin, V. Pronin, V. Ryltsev, S. Sturchak and V. Filatov. Briefly, polycaproamide was activated by hydrolysis in 3M aqueous HCl at room temperature for 15 hours (1:15, w:v). The activated polycaproamide was then washed extensively with distilled water. The washed polymer was then placed for 15 h at room temperature in 5% (w/v) glutaraldehyde aqueous solution (1:10, w:v). The formed aldehyde-polycaproamide was then washed extensively with distilled water. Coupling of trypsin to the activated aldehyde-polycaproamide was performed according to the procedure described previously for coupling trypsin to dialdehyde cellulose. In these studies, home-made PAKS-TRYPSIN and the commercial product gave similar results.

Sterilization. Each air-dried polymeric dressing (100 mg) was hermetically packed in a nylon and sterilized by cobalt irradiation (2.5 Mrad)

BURN WOUNDS AND TREATMENT

The skin on the back and both sides of each guinea pig was prepared for wounding by hair removal with a shaver, hair removing cream and then washing the skin with water. Soap and antiseptics were not used because of their potential influence on the wound healing process. Burn wounds were made according to the methodology of S. C. Davis, P. P. Mertz and W. H. Eaglstein, J. Surg. Res., 48, 245 (1990). On the day of burning, the guinea pigs were anesthetized with ether according to the methodology of J. S. Paterson in "The UFAW Handbook on Care and Management of Laboratory Animals", Ed. by UFAW, 223–241 (1972).

Animals were placed in a ventilated glass container with a pad soaked in ether. Care has been taken that the pad does not touch the animal, as ether burns mucous membranes. The animals can thus be observed and be withdrawn when the desired stage is reached.

Two specially designed brass rods weighing 45 g each were heated to 120° C. precisely. The brass rods were held perpendicularly at the same time on the both sides of the back skin of the guinea pig, with all pressure supplied by gravity, for 15 seconds, to make a burn wound of 10×20 mm diameter and 0.7 mm deep. Thus, on each animal 2 burn wounds were made (on the left and right sides of the back)—one for treatment by control bandage and the other for treatment by bioactive conjugated bandage.

The Examples which follow illustrate the present invention.

FIG. 7 having shown that major differences existed between the known and present activation methods for coupling bioactive compounds, e.g. proteins, to polysaccharides, e.g. cellulose, through hydroxyl groups, a detailed example of both activation methods is now provided.

EXAMPLE 1

Preparations of activated cellulose by the known and new methods

A. Known activation method of cellulose with tosyl chloride.

1 g cellulose (medical gauze), treated by boiled $NaHCO_3$ and/or 0.05N NaOH as previously described, was washed with 10 ml of water. The water was then removed by drying at 105° C./or by washing with water/acetone (3:1, v/v), water/acetone (1:3, v/v), acetone and finally with dried acetone. The cellulose was then transferred to a flask containing 10 g tosyl chloride dissolved in 10 ml dried acetone. During shaking, 2 ml pyridine was added dropwise for about 1 min. After a 1-h reaction at room temperature, the cellulose was washed extensively with dried acetone and then air dried/or transferred back to water by reversing the washing scheme described above.

B. Present activation method of cellulose with tosyl chloride.

1 g dried cellulose (and/or native cellulose containing approximately 6% humidity), medical gauze, was soaked in 2 ml pyridine at room temperature for approximately 30 min. The pretreated pyridine swelled cellulose was then transferred to a flask containing 10 g tosyl chloride dissolved in 10 ml dried acetone. After a 1-h reaction at room temperature, the cellulose was washed extensively with dried acetone and then air dried/or transferred to aqueous solution as described previously. The amount of bound tosyl groups was 0.125 mmol/g cellulose, corresponding to 0.020 tosyl groups per monosaccharide unit (Mn-162), for cellulose activated by the known method and increased by 25 fold, up to 3.12 mmol/g cellulose, or 0.50 tosyl group per monosaccharide unit, for cellulose activated by the new method. Coupling trypsin to tosylated cellulose.

Figure 9:
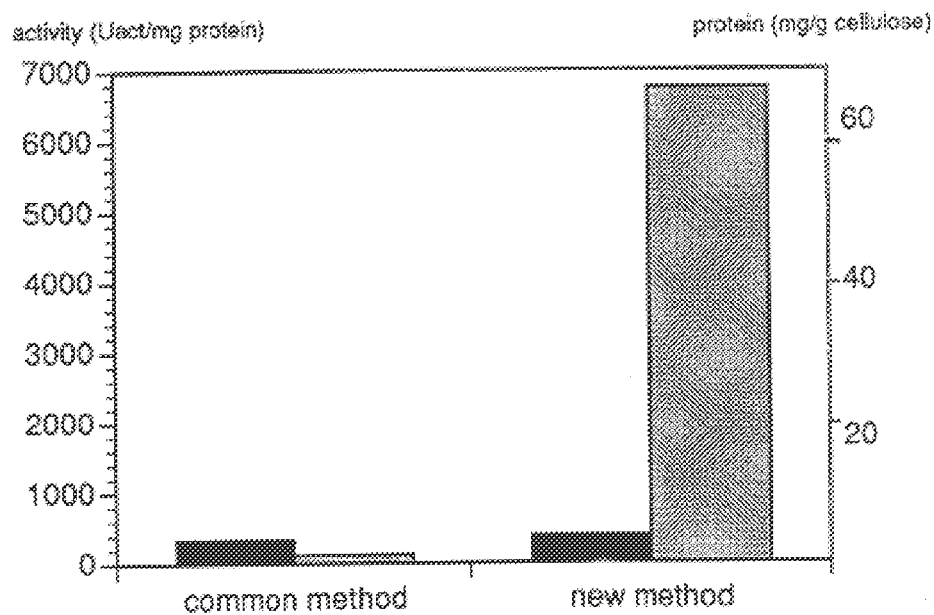
FIG. 9 compares the quantity and activity of trypsin coupled to tosylated cellulose formed by the known method and in accordance with an embodiment of the invention.

1 g of tosylated cellulose formed by either the known or new activation methods was soaked at room temperature for 18 h in 2.5 ml of 0.1M aqueous bicarbonate buffer, pH 8.5 containing 0.5% trypsin (w/v). Unbound trypsin of each sample was then washed with 50 ml of the bicarbonate buffer and then with 5×50 ml saline (0.85% NaCl in water). Residual tosyl groups were then removed by soaking the obtained samples at room temperature for 1 h in 0.05 M carbonate buffer, pH 11. The derivatized cellulose samples were then washed with 50 ml carbonate buffer, 5×50 ml saline, 50 ml distilled water and then air-dried at room temperature. The amount of coupled trypsin was similar for cellulose activated by both known or new methods, but the enzyme activity of cellulose activated by the new method was approximately 9-fold higher. (FIG. 9).

EXAMPLE 2

Example 1-B (new activation method) was repeated substituting soaking of 1 g cellulose in 2 ml pyridine for soaking cellulose in increased amount of pyridine, i.e. >2 ml. Similar results were obtained. (It is also be noted that 1 g cellulose is not completely wetted by less than 2 ml pyridine). Similar results were also obtained when the pre-treatment of cellulose in pyridine was effected for >30 min. On the other hand, pre-treatment for <30 min. resulted in a slightly lower amount of cellulose bound tosyl groups and trypsin.

EXAMPLE 3

Activation of cellulose powder

Figure 10:
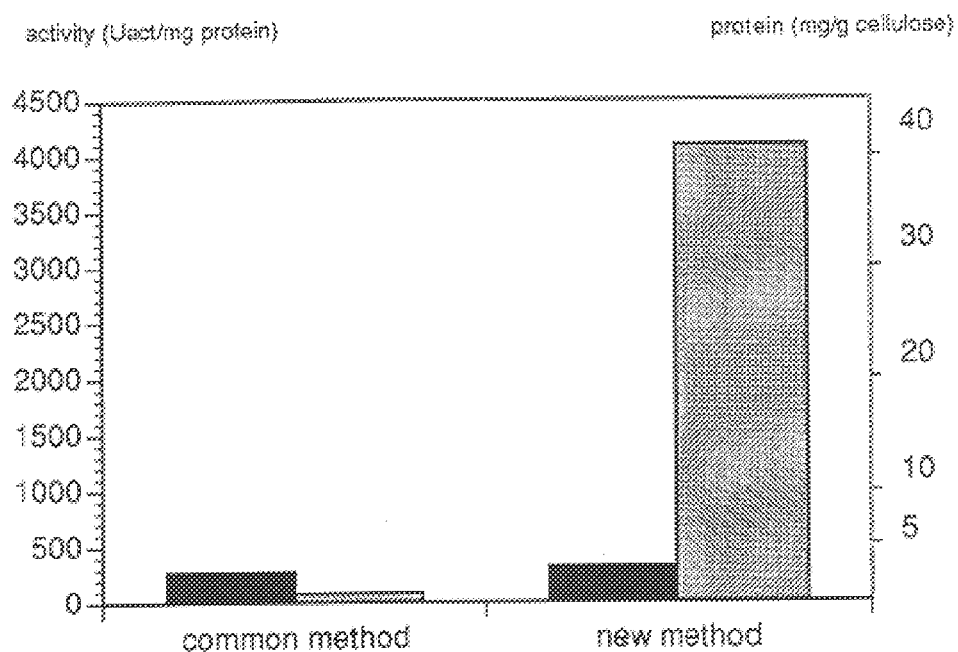
FIG. 10 compares the quantity and activity of trypsin coupled to tosylated cellulose powder formed by the known method and in accordance with an embodiment of the invention.

Examples 1–2 were repeated substituting textile cellulose (medical gauze) for cellulose powder. The amounts of trypsin coupled to the powdered cellulose activated by the known and new methods and their enzyme activity were similar to that obtained for the textile cellulose, Example 1, (FIG. 10).

EXAMPLE 4

Activation of cellulose by tresyl chloride

Figure 11:
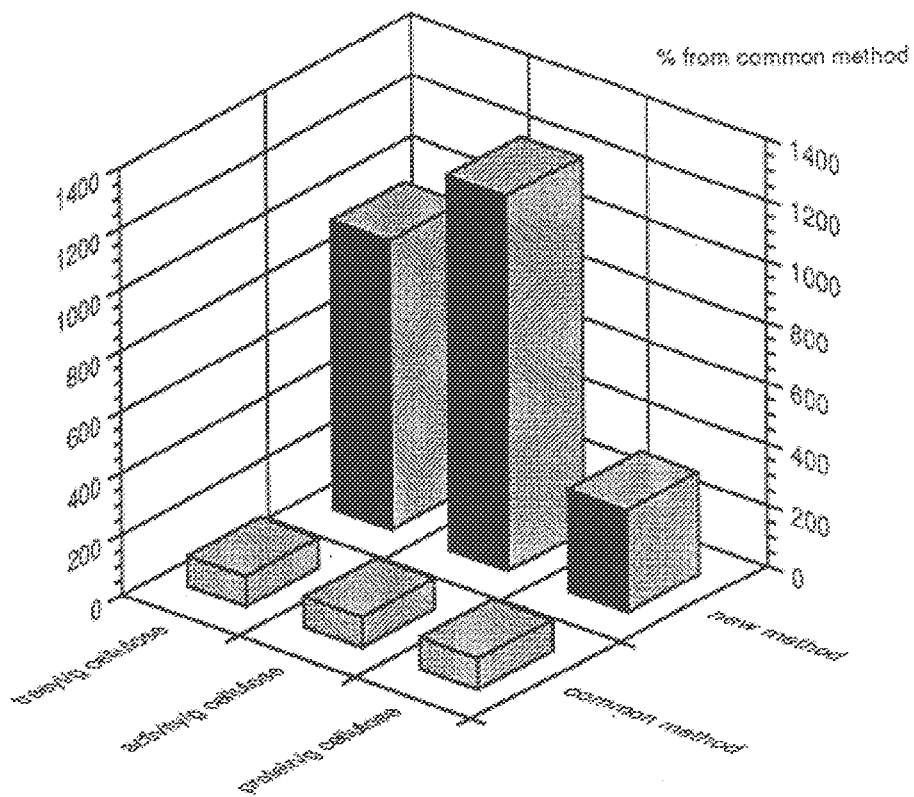
FIG. 11 compares the quantity of tresyl groups, and the quantity and activity of trypsin coupled to tresylated cellulose, formed by the known method and in accordance with an embodiment of the invention.

Examples 1–3 were repeated substituting the activating agent tosyl chloride for tresyl chloride (50 ml for 1 g of cellulose). A comparison between the known activation method and the new one with regard to the amount of tresyl groups and trypsin molecules coupled to cellulose and the activity of the bound trypsin is demonstrated in FIG. 11. Both, the quantity of tresyl groups and quantity of coupled trypsin, as well as its activity were significantly higher for cellulose activated by the new activation method compared to the known one.

EXAMPLE 5

Variation of solvents
A. Solvents for cellulose activation.
Examples 1–4 were repeated substituting acetone for 1,4-dioxane. Similar results were obtained.
B. Solvents for pre-treatment of cellulose.
Samples containing 1 g cellulose were pre-treated by soaking at room temperature for 1 h in acetone and/or 1,4-dioxane. The cellulose samples, either in the swelled state or in the dry state, were then treated as described in Examples 1–4. Similar results were obtained.

EXAMPLE 6

Variation in cellulose pre-cleaning procedure 1 g cellulose was treated by soaking in boiled $NaHCO_3$ and/or 0.05N NaOH (mercerization) as previously described. Examples 1-B and 3 (new activation method) were then repeated. Similar results were obtained.

EXAMPLE 7

Variation of pyridine concentration

Figure 12:
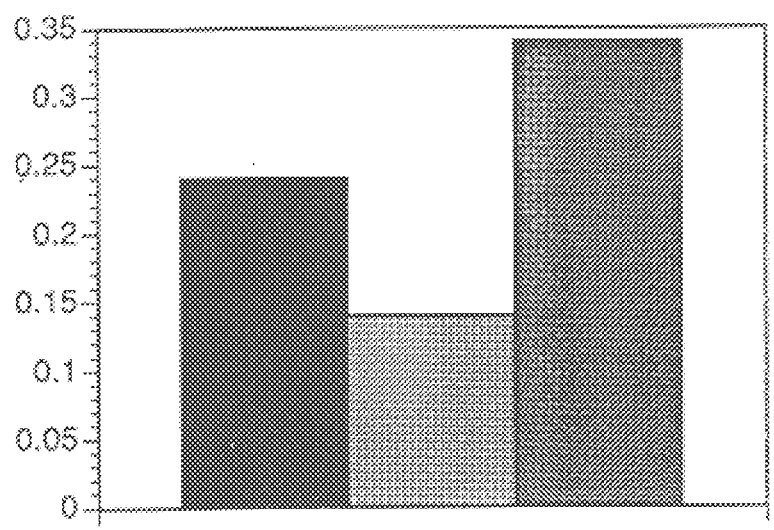
FIG. 12 compares the quantity of tosyl groups coupled to cellulose formed by variation in pyridine concentration in the known activation method.

Example 1-A (known activation method) was repeated substituting soaking of cellulose in 10 ml acetone and 2 ml pyridine (17% pyridine in acetone) with solutions of A. 50% pyridine in acetone (6 ml acetone+6 ml pyridine) and B. 100% dried pyridine. The quantity of tosyl groups coupled to cellulose was higher for 100% pyridine than for 50% pyridine (0.075 mmol/g compared to 0.059 mmol/g, respectively), but lower than that obtained in the known activation method described in Example 1-A, 0.125 mmol/g, (FIG. 12).

EXAMPLE 8

Effect of pyridine pre-treatment on the interaction between trypsin and cellulose The effect of pyridine on the binding of bioactive reagents, e.g. proteins, to cellulose has been studied by the following trials:
(a) Example 1-A (known activation method) was repeated without addition of pyridine to acetone.
(b) 1 g cellulose was soaked at room temperature for 30 min. in 2 ml pyridine. The cellulose was then washed extensively with acetone and then air dried. Then, (a) was repeated.
(c) Example 1-A was repeated.
(d) 1 g cellulose was soaked at room temperature for 30 min. in 2 ml pyridine. The cellulose was then washed extensively with acetone and then air dried. Then Example 1-A was repeated.
(e) Example 1-B (new activation method) was repeated.

Figure 13:
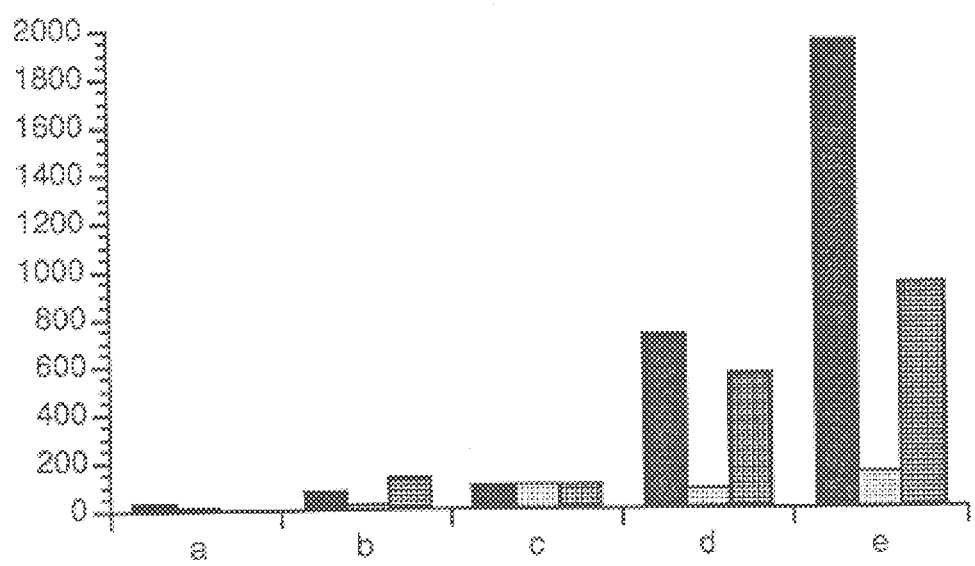
FIG. 13 compares the effect of cellulose pre-treatment with pyridine on the quantity of bound tosyl groups and on the quantity and activity of trypsin coupled to tosylated cellulose.
Figure 14:
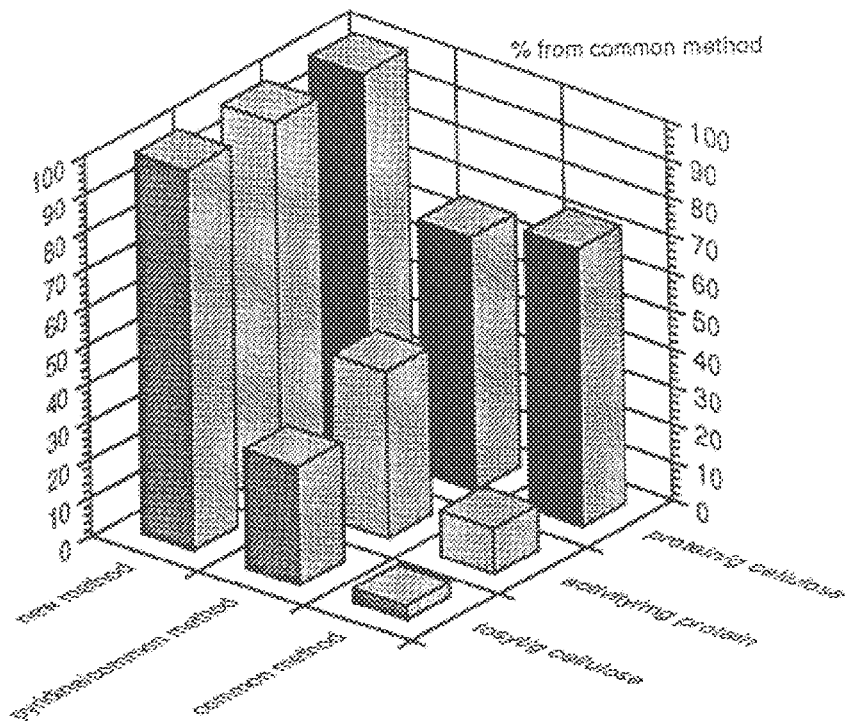
FIG. 14 shows the effect of the activation method in accordance with an embodiment of the invention on the quantity of coupled tosyl groups and quantity and activity of coupled trypsin.

The activated cellulose formed in the different ways was then interacted with trypsin according to the procedure described in Example 1. FIG. 13–14 demonstrate that the amount of the bound tosyl groups and the activity of the coupled trypsin is according to the following order: e>d>c>b>a. These Figures clearly show the relative increase in the amount of bound trypsin and the increase in the activity of the bound enzyme due to the pre-treatment of cellulose in pyridine. These Figures also indicate that the highest amount of bound tosyl groups and the highest enzyme activity of the coupled trypsin were obtained by the new activation method described in Example 1-B.

EXAMPLE 9

Figure 15:
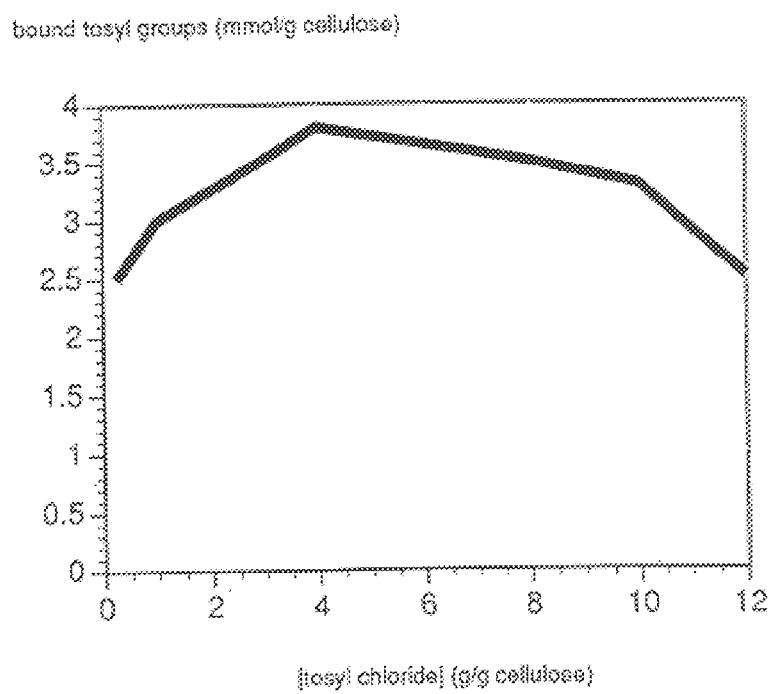
FIG. 15 depicts the effect of tosyl chloride concentration on the quantity of tosyl groups bound to cellulose.

Effect of initial tosyl chloride concentration on the amount of coupled tosyl groups Example 1-B was repeated for different concentrations of tosyl chloride in acetone (0.25, 1, 4, 8, 10, 12 g/10 ml acetone). FIG. 15 demonstrates that the highest amount of bound tosyl groups is obtained for initial tosyl chloride concentration of 4 g/10 ml acetone.

EXAMPLE 10

Figure 16:
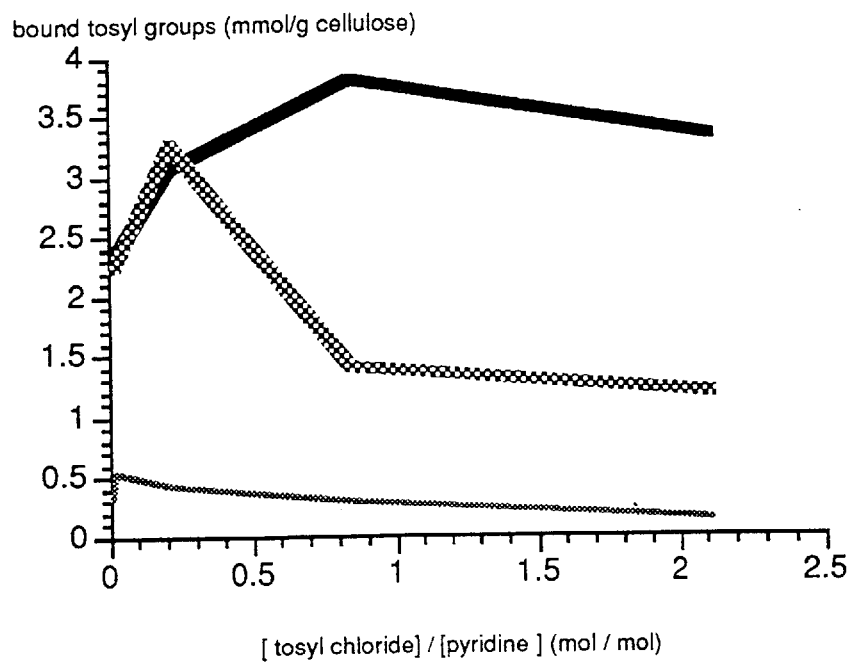
FIG. 16 depicts the effect of the tosyl chloride/pyridine molar ratio on the quantity of tosyl groups coupled to cellulose.

Effect of the initial molar ratio [tosyl chloride]/[pyridine] on the amount of bound tosyl groups Examples 1 (known and new activation methods) and 8-d (cellulose pre-treated with pyridine, washed then from excess pyridine with acetone and then activated by the known activation method) were repeated with different molar ratios of [tosyl chloride]/[pyridine] (1:70, 1:50, 1:5, 1:1, 2:1 tosyl chloride/pyridine, mol/mol). FIG. 16 demonstrates that the lowest amount of bound tosyl groups is always obtained by the known activation method. However, for initial molar ratios of [tosyl chloride]/[pyridine] up to approximately 0.25, similar amounts of bound tosyl groups were obtained by the new activation method and the method described in Example 8-d. On the other hand, for initial molar ratios of [tosyl chloride]/[pyridine] above approximately 0.25, the amount of bound tosyl groups was significantly higher in the new activation method relative to the method described in Example 8-d.

EXAMPLE 11

Effect of organic bases, others than pyridine, on the interaction between trypsin and cellulose Example 1 was repeated substituting pyridine with triethylamine and/or propylamine. Table 1 demonstrates the significant superiority of pyridine on triethylamine and propylamine in the new activation method, i.e. the obtained activity of the bound trypsin was 6720 Uact/mg protein for pyridine, 874 Uact/mg protein for triethylamine and ☉ Uact/mg protein for propylamine. On the other hand, in the known activation method the differences in the activity of the bound trypsin due to the change in the organic bases do not exist or significantly reduced, i.e. The obtained bound trypsin activity was 743 Uact/mg protein for pyridine, 765 Uact/mg protein for triethylamine and 167 Uact/mg protein for propylamine.

TABLE 1

Effect of organic bases on the binding of trypsin to cellulose.

| Activation: Organic base | Quantity of bound tosyl groups (mmol/g cellulose) | | Protein-binding capacity of tosylated cellulose | | | |
|---|---|---|---|---|---|---|
| | | | Quantity of bound trypsin (mg/g cellulose) | | Enzyme activity of bound trypsin (Uact/mg protein) | |
| | Known method | Present method | Known method | Present method | Known method | Present method |
| Pyridine | 0.120 | 3.120 | 3.0 | 3.8 | 743 | 6720 |
| Triethylamine | 0.019 | 0.058 | 1.7 | 5.2 | 765 | 874 |
| Propylamine | 0.011 | 0.056 | 0.5 | 0.2 | 167 | 0 |

EXAMPLE 12

Effect of various N-heterocyclic compounds on the interaction between trypsin and cellulose Example 1 was repeated, using instead of pyridine the following: piperidine, pyridazine, pyrrolidine, pyrroline and pyrrole. Table 2 demonstrates the significant superiority of the new method of activation over the known method, as indicated by the similar or greater quantity of bound tosyl groups, and the greater quantity and activity of bound trypsin.

TABLE 2

Effect of N-heterocyclic bases on the binding of trypsin to cellulose.

| Activation: Organic base | Quantity of bound tosyl groups (mmol/g cellulose) | | Protein-binding capacity of tosylated cellulose | | | |
|---|---|---|---|---|---|---|
| | | | Quantity of bound trypsin (mg/g cellulose) | | Enzyme activity of bound trypsin (Uact/mg protein) | |
| | Known method | Present method | Known method | Present method | Known method | Present method |
| Piperidine | 0.06 | 0.1 | 1.28 | 1.38 | 1260 | 2666 |
| Pyridazine | 0.25 | 1.67 | 2.65 | 47.70 | 4380* | 45390* |
| Pyrrolidine | 0.15 | 0.54 | 0.78 | 1.20 | 740 | 2400 |
| Pyrroline | 0.09 | 0.2 | 2.17 | 2.19 | 1940 | 2460 |
| Pyrrole | 0.11 | 0.11 | 2.18 | 2.58 | 440 | 2380 |

*Uact/g cellulose

EXAMPLE 13

Examples 1 and 12 (in part) were repeated, replacing trypsin by albumin. Table 3 demonstrates the significant superiority of the new method of activation over the known method, as indicated by the greater quantity and activity of bound albumin.

TABLE 3

Effect of N-heterocyclic bases on the binding of albumin to cellulose.

| Activation: Organic base | Quantity of bound albumin (mg/g cellulose) | | Activity of bound albumin (% bilirubin absorbed from solution) | |
|---|---|---|---|---|
| | Known method | Present method | Known method | Present method |
| Pyridine | 1.81 | 2.63 | 11.3 | 54.1 |
| Pyridazine | 2.31 | 5.62 | 29.5 | 51.8 |
| Pyrrole | 0.25 | 0.39 | 5.7 | 14.7 |

EXAMPLE 14

Examples 1 and 12 (in part) were repeated, replacing cellulose by agarose. Table 4 demonstrates the significant superiority of the new method of activation over the known method, in the case of agarose, as indicated by the greater quantity of bound tosyl groups, and the greater quantity and activity of bound trypsin.

TABLE 4

Effect of N-heterocyclic bases on the binding of trypsin to agarose.

| Activation: Organic base | Quantity of bound tosyl groups (mmol/g agarose) | | Protein-binding capacity of tosylated agarose | | | |
|---|---|---|---|---|---|---|
| | | | Quantity of bound trypsin (mg/g agarose) | | Enzyme activity of bound trypsin (Uact/mg protein) | |
| | Known method | Present method | Known method | Present method | Known method | Present method |
| Pyridine | 0.10 | 0.90 | 1.06 | 2.13 | 648 | 1003 |
| Pyridazine | 0.37 | 2.06 | 3.41 | 4.30 | 1050 | 3241 |

EXAMPLE 15

Effect of pyridine post-treatment on the interaction between trypsin and cellulose The new activation method described in Example 1-B was repeated. The formed dried tosyl activated cellulose was then retreated with pyridine by re-soaking at room temperature for 1 h in pyridine. The purpose of this post-retreatment with pyridine is to substitute part of tosyl groups of the tosylated cellulose with bound pyridine. The derivatized cellulose was then extensively washed with acetone and dried then at room temperature. The amount of bound tosyl groups decreased by this procedure by twice (from 3.12 mmol/g cellulose to 1.47 mmol/g cellulose).

In order to remove further residual tosyl groups after the post-treatment with pyridine, the derivatized cellulose was soaked at room temperature for 1 h in 10 ml 0.05M aqueous bicarbonate buffer at pH 11. The derivatized cellulose was then washed extensively with water and then air dried. Coupling of trypsin to the derivatized pyridine post-treated cellulose was then accomplished according to the description in Example 1.

The amount of coupled trypsin decreased significantly by the pyridine post-treatment (0.5 mg/g cellulose instead of 3.8 mg/g cellulose), but the activity of the bound enzyme increased significantly (from 6744 Uact/mg protein to 10242 Uact/mg protein).

Similar results were obtained if the post-treatment with pyridine was accomplished at temperatures higher than 25° C.

EXAMPLE 16

Influence of pH on trypsin coupling to tosylated cellulose 3 g of tosylated cellulose prepared according to Example 1-B (new activation method) was divided into 3 pieces of 1 g each. Each piece was shaken at room temperature for 18 h in 2.5 ml of trypsin aqueous solution (0.5%, w/v) in the following aqueous buffers:
A. K/Na phosphate buffer, 0.1 M, pH 7.5.
B. NaHCO3 buffer, 0.1 M, pH 8.5.
C. NaHC03 buffer, 0.1 M, pH 9.7.

Table 5 demonstrates that the amount of bound trypsin was similar in all buffers, but the enzyme activity was the highest for carbonate buffer at pH 8.5.

TABLE 5

Influence of pH on the binding of trypsin to tosylated cellulose.

| Buffer | | Quantity of bound trypsin (mg/g cellulose) | Enzyme activity of bound trypsin (Uact/mg protein) |
|---|---|---|---|
| Phosphate | 0.1 M pH 7.5 | 11.6 | 3435 |
| Carbonate | 0.1 M pH 8.5 | 3.8 | 6700 |
|  | pH 9.7 | 4.4 | 4189 |

EXAMPLE 17

Effect of temperature on trypsin coupling to tosylated cellulose

Example 16-B was repeated at the following temperatures:
A. 4° C.
B. 25° C.
C. 40° C.

Table 6 demonstrates similar binding capacity and enzyme activity at 4° C. and at 25° C. On the other hand, at 40° C. similar binding capacity was obtained, but due to denaturation the bound enzyme completely lost its activity.

TABLE 6

Effect of temperature on the binding of trypsin to tosylated cellulose.

| Temperature (°C.) | Quantity of bound trypsin (mg/g cellulose) | Enzyme activity of bound trypsin (Uact/mg protein) |
|---|---|---|
| 4 | 3.3 | 6747 |
| 25 | 3.8 | 6760 |
| 40 | 2.7 | 0 |

EXAMPLE 18

Kinetics of trypsin coupling to tosylated cellulose

Example 17-B was repeated at different interval of incubation time of the tosylated cellulose with trypsin solution.

Figure 17:
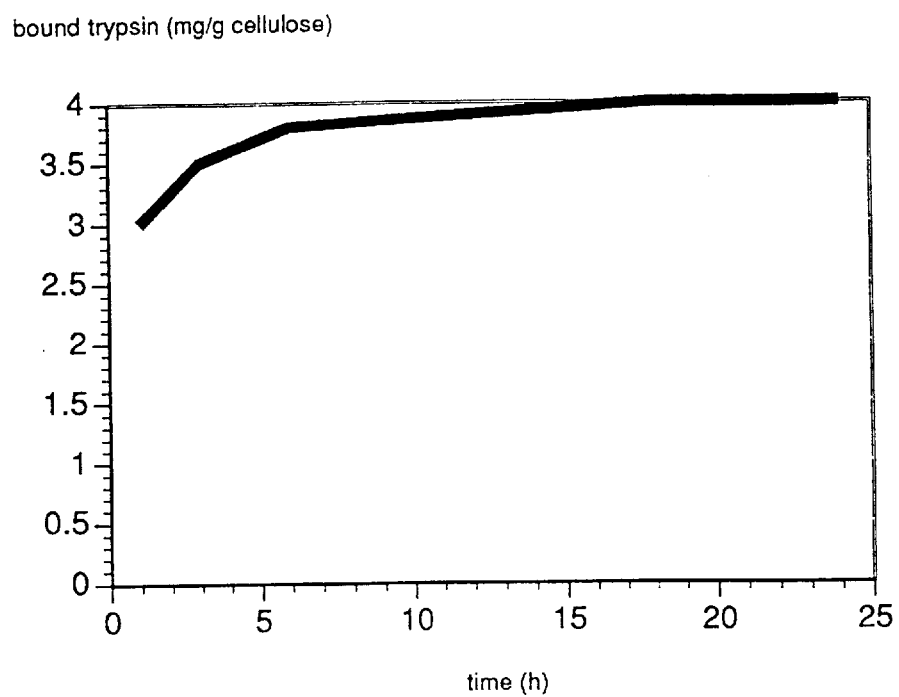
FIG. 17 depicts the kinetics of trypsin binding to tosylated cellulose.

The results demonstrated in FIG. 17 show that under these experimental conditions after approximately 6 h, or more, maximum trypsin binding was reached.

EXAMPLE 19

Effect of trypsin concentration on its binding to tosylated cellulose

Figure 18:
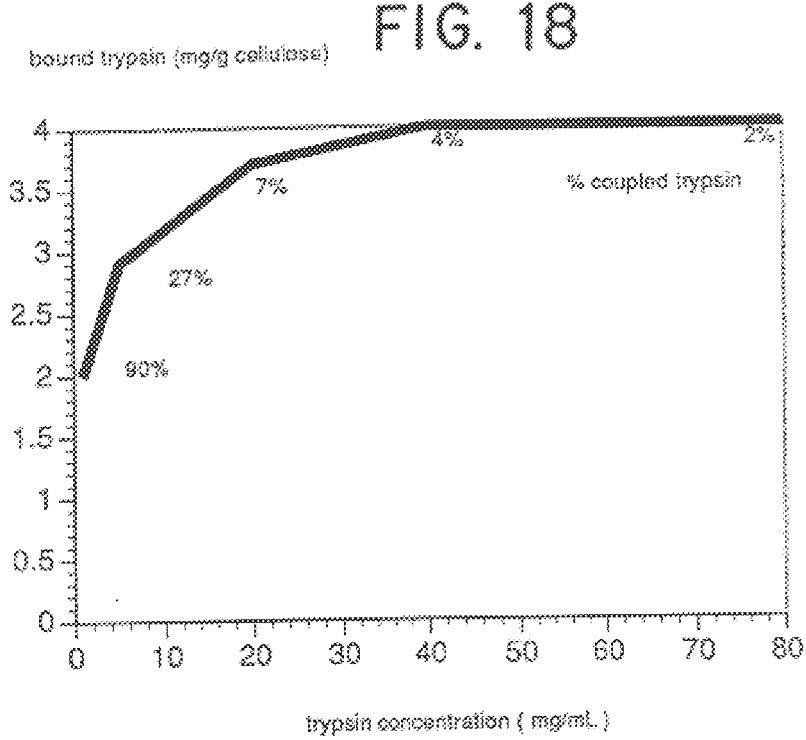
FIG. 18 depicts the effect of trypsin concentration on its binding to tosylated cellulose.

Example 18 was repeated at the following trypsin concentrations:
A. 1 mg/ml
B. 5 mg/ml
C. 20 mg/ml
D. 40 mg/ml
E. 80 mg/ml FIG. 18 demonstrates that the maximum amount of coupled trypsin was reached for initial trypsin concentration of 40 mg/ml, or more, i.e. 4 mg/g cellulose. However, under these experimental conditions, e.g. initial trypsin concentration of 40 mg/ml, the percent of trypsin coupled to cellulose is relatively low, i.e. 4% for initial trypsin concentration of 40 mg/mi. On the other hand, at relatively lower initial trypsin concentration the percent trypsin coupled to cellulose is relatively higher, i.e. at initial trypsin concentration of 5 mg/ml the percent of trypsin coupled to cellulose was 27%.

EXAMPLE 20

Effect of various hydrolyzing reagents on the binding of trypsin to tosylated cellulose Example 1-B (new activation method and then trypsin coupling) was repeated in presence of the following reagents which aim to hydrolyze residual tosyl groups coupled to cellulose:
A. 0.2M Tris buffer, pH 11.
B. 0.1M Tris buffer, pH 8.
C. 0.05M NaHCO3 buffer, pH 11.
D. 0.1% ethanolamine+HCl, pH 8.
E. 0.8M mercaptoethanol+NaOH, pH 8.

Table 7 demonstrates that the highest amount of coupled trypsin and enzyme activity was obtained at the presence of 0.05M NaHCO3 aqueous buffer, pH 11.

TABLE 7

Effect of various hydrolyzing reagents on the binding of trypsin to tosylated cellulose.

| Hydrolyzing conditions | Quantity of bound trypsin (mg/g cellulose) | Enzyme activity of bound trypsin (Uact/mg protein) |
|---|---|---|
| Tris 0.2 M, pH 11 | 2.5 | 2636 |
| Tris 0.1 M, pH 8 | 3.3 | 5053 |
| NaHCO$_3$ 0.05 M, pH 11 | 3.8 | 6744 |
| Ethanolamine 0.15 M, pH 8 | 3.4 | 2108 |
| Mercaptoethanol 0.8 M, pH 8 | 1.8 | 0 |

EXAMPLE 21

Coupling of enzymes others than trypsin to cellulose by the new and known activation methods Example 1 was repeated substituting the proteolytic enzyme trypsin with the following enzymes:

A. collagenase.
B. lysozyme.
C. hyaluronidase.

Figure 19:
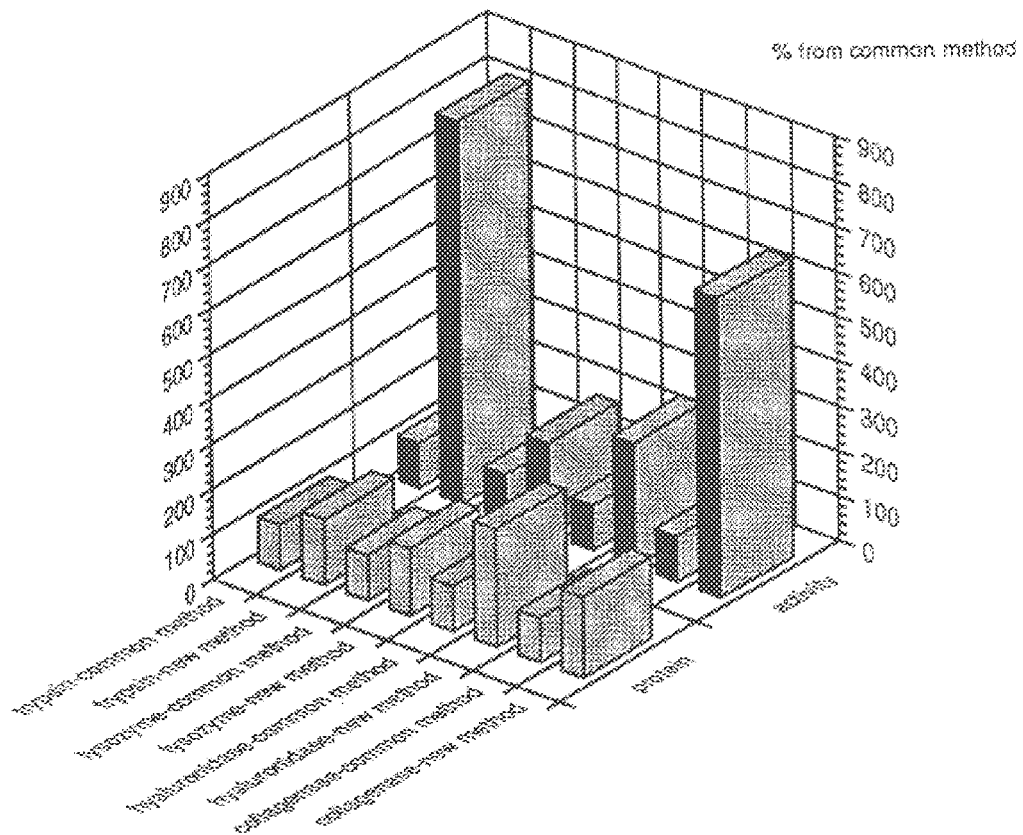
FIG. 19 depicts the quantity and activity of various enzymes coupled to tosylated cellulose formed by the known activation method and a method in accordance with an embodiment of the invention.

FIG. 19 shows that in both activation methods, the known method and the new one, the amounts of coupled enzymes (collagenase, lysozyme and hyaluronidase) to cellulose was similar. However, the activity of the bound enzymes was significantly higher for the enzymes coupled to cellulose by the new activation method.

EXAMPLE 22

Consecutive coupling of enzymes to cellulose via the new and known activation methods 1 g tosylated cellulose formed by the known and new activation methods, as described in Example 1, was soaked at room temperature for 0.5 h in 2.5 ml of 0.1M aqueous bicarbonate buffer, pH 8.5 containing 0.5% trypsin (w/v). 2.5 ml of collagenase solution (5 mg/ml in 0.1M NaHC03 buffer, pH 8.5) was then added and the reaction continued for another 17.5 h. Washing of unbound enzymes was then accomplished according to Example 1.

A comparison between the quantity and activity of the enzymes bound separately (according to Examples 1 and 21-A) and consecutively is shown in Table 8.

TABLE 8

Quantity and activity of enzymes bound separately or consecutively totosylated cellulose formed by the new and known activation methods.

| Enzyme | Quantity (mg/g cellulose) | | Enzyme activity (Uact/mg protein) | |
| --- | --- | --- | --- | --- |
| | Coupling | Consec. coupling | Coupling | Consec. coupling |
| Trypsin | 3.8 | 3.2 | 6700 | 6865 |
| Collagenase | 5.2 | 4.3 | 1176 | 1365 |

EXAMPLE 23

Example 21 was repeated substituting textile cellulose (medical gauze) for cellulose powder. Similar results were obtained.

EXAMPLE 24

Example 22 was repeated substituting the collagenase solution with a solution containing 3 enzymes: collagenase, lysozyme and hyaluronidase (5 mg/ml of each enzyme in 2.5 ml of 0.1M NaHCO buffer at pH 8.5).

Figure 20:
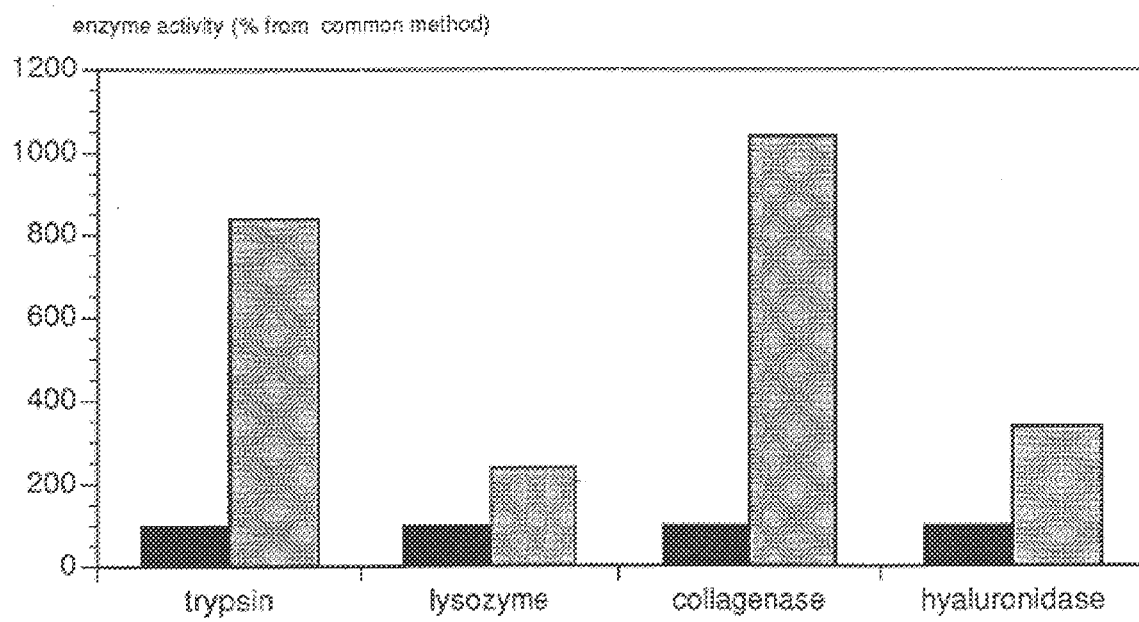
FIG. 20 depicts the activity of enzymes consecutively coupled to tosylated cellulose formed by the known activation method and a method in accordance with an embodiment of the invention.

FIG. 20 demonstrates the significant higher activity of the enzymes coupled to tosylated cellulose prepared by the new activation method compared to the known activation method.

EXAMPLE 25

Effect of pre-treatment of dialdehyde cellulose with organic solvents on trypsin binding and activity of the bound enzyme 1 g dialdehyde cellulose was soaked for 30 min. at room temperature in 2 ml pyridine. The dialdehyde cellulose was then washed with 6×50 ml acetone and then air dried. Coupling of trypsin to the pyridine pre-treated dialdehyde cellulose was then accomplished as described in materials and methods.

Similar trials were carried out by soaking the dialdehyde cellulose with acetone or dioxane instead of pyridine.

Table 9 demonstrates that the binding and activity of the bound trypsin did not change significantly by the pretreatment of the dialdehyde cellulose with the above solvents.

TABLE 9

Effect of pre-treatment of dialdehyde cellulose (DAC) with organic solvents on trypsin binding and activity of the bound enzyme

| Pre-treatment | Quantity of bound trypsin (mg/g DAC) | Enzyme activity of bound trypsin (Uact/mg protein) |
| --- | --- | --- |
| — | 3.4 | 616 |
| Acetone | 4.2 | 652 |
| Dioxane | 3.2 | 665 |
| Pyridine | 4.8 | 714 |

EXAMPLE 26

Figure 21:
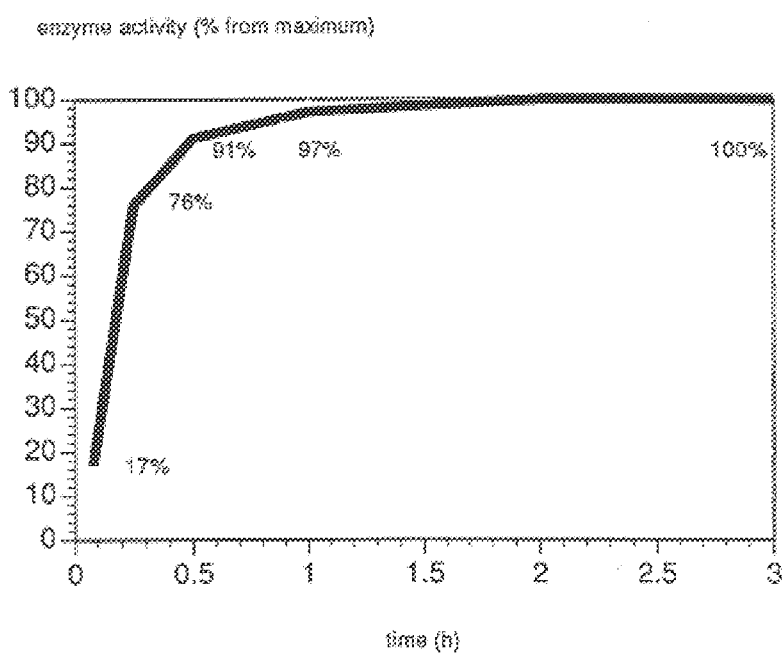
FIG. 21 shows the time required for reaching complete enzyme activity of dried cellulose-trypsin conjugates.

Time required for reaching complete enzyme activity of dried cellulose-trypsin conjugates Dried samples of trypsin-cellulose conjugates prepared according to Example 1 were wetted by soaking at room temperature in 0.1M K/Na phosphate buffer, pH 7.5, 1:10 (w:v). FIG. 21 demonstrates that after approximately 1 h in the aqueous solution the enzyme reached its complete activity.

EXAMPLE 27

A comparison in the degree of hygroscopicity of different activated polymers prepared for wounds treatment Table 10 demonstrates the relative hygroscopicity of the following activated polymers prepared for wounds treatment:

A. Dialdehyde cellulose prepared according to the description in materials and methods.
B. Dialdehyde cellulose pre-treated with different solvents (acetone, dioxane and pyridine) according to Example 25.
C. Polycaproamide-glutaraldehyde prepared according to the description in materials and methods.
D. Tosylated cellulose prepared according to the known activation method (Example 1-A).
E. Tosylated cellulose pre-treated with pyridine, prepared according to the new activation method (Example 1-B)
F. Tosylated cellulose pre-treated and post-treated with pyridine, prepared according to Example 15.

Table 10 demonstrates that the highest degree of hygroscopicity was obtained for tosylated cellulose pre-treated with pyridine according to the new activation method and for tosylated cellulose pre-and post-treated with pyridine.

TABLE 10

Relative hygroscopicity of different activated polymers.

| Activated polymer | Pre-treatment | Hygroscopicity (% from cellulose) |
|---|---|---|
| Dialdehyde cellulose | — | 94 |
| | acetone | 106 |
| | dioxane | 117 |
| | pyridine | 126 |
| Polycaproamide-glutaraldehyde | — | 81 |
| Tosylated-cellulose | — | |
| | (known activation method) | 218 |
| | pyridine (new activation method) | 376 |
| | pyridine (pre- and post-treatment) | |

EXAMPLE 28

Stability and activity of enzyme-coupled polymers 25 mg of each of the following conjugated polymers were placed at room temperature in 0.25 ml of 0.1M K/Na aqueous phosphate buffer at pH 7.5.

A. Trypsin coupled to cellulose prepared according to the new and/or known activation methods described in Example 1.
B. Trypsin coupled to dialdehyde cellulose (DALCEKS-TRYPSIN) prepared according to the description in materials and methods.
C. Trypsin coupled to polycaproamide (PAKS-TRYPSIN) prepared according to the description in materials and methods.

Figure 22:
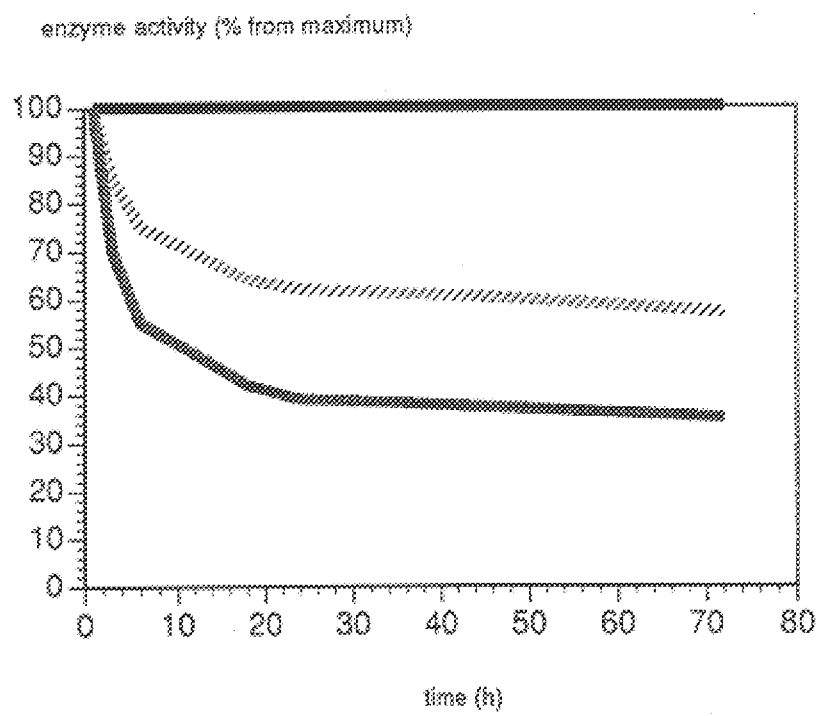
FIG. 22 illustrates activity of trypsin bound to different polymers as a function of time.

FIG. 22 demonstrates that the activity of trypsin coupled to cellulose according to the new and/or known activation methods did not change during time. On the other hand, a significant decrease in activity during time of trypsin coupled to dialdehyde cellulose and/or polycaproamide has been observed. Furthermore, bound trypsin leached from the polymers into the aqueous solution of the conjugated cellulose prepared according to the new and/or known activation methods was not detected. On the other hand, significant amount of free trypsin and/or trypsin bound to water soluble polymers was observed for PAKS-TRYPSIN and for DALCEKS-TRYPSIN.

EXAMPLE 29

Sterilization of the bioactive conjugated polymers

The following air-dried bandages, containing each 100 mg bioactive conjugated polymer hermetically packed in a nylon bag, have been sterilized by 2.5 Mrad gamma radiation:
A. Cellulose (control)
B. Trypsin coupled to dialdehyde cellulose (DALCEKS-TRYPSIN) prepared according to the description in materials and methods.
C. Trypsin coupled to polycaproamide (PAKS-TRYPSIN) prepared according to the description in materials and methods.
D. Trypsin coupled to cellulose prepared according to the new and/or known activation methods described in Example 1.
E. Trypsin coupled to cellulose pre-treated and post-treated with pyridine, prepared according to Example 15.
F. Trypsin and collagenase coupled to cellulose, prepared according to Example 22.

Figure 23:
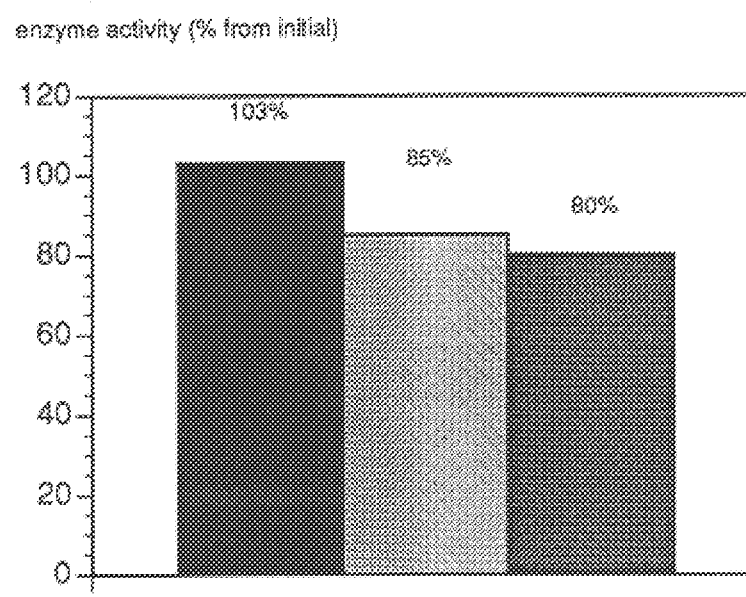
FIG. 23 depicts enzyme activity of trypsin conjugated polymers after sterilization by gamma-irradiation.

FIG. 23 demonstrates that the activity of trypsin coupled to dialdehyde cellulose (DALCEKS-TRYPSIN) and/or to polycaproamide (PAKS-TRYPSIN) decreased significantly by the sterilization procedure. On the other hand, the activity of the enzymes coupled to cellulose by the new activation method and/or known activation method and/or by the pre-and post-treatment with pyridine did not change significantly by the gamma sterilization process.

EXAMPLE 30

Sterilization of the bioactive conjugated polymers

Air dried bandages prepared as described in Example 24, each containing 100 mg bioactive conjugated polymer, and hermetically packed in a laminated polyester/aluminum/polyethylene bag, were sterilized by 3.0 Mrad gamma irradiation, while keeping in a Dewar containing liquid nitrogen or solid $CO_2$, in an inert atmosphere of nitrogen or $CO_2$, respectively.

The data presented in Table 11 show that the activity of the enzymes coupled to cellulose in the multienzyme dressings, in accordance with an embodiment of the invention, was retained after irradiation at low temperatures. On the other hand, the activity of enzymes bound to cellulose according to the known method was significantly decreased by irradiation. For example, the activity of lysozyme bound to cellulose by the known method retained only 31% of its original activity after irradiation, whereas using the present method there was no loss of lysozyme activity after irradiation.

TABLE 11

Relative activity of bound enzymes in multienzyme dressings after irradiation

| Bound enzyme | Bound enzyme activity Known method | (initial activity = 100) Present method |
|---|---|---|
| Trypsin | 80 | 105 |
| Lysozyme | 31 | 105 |
| Collagenase | — | 100 |
| Hyaluronidase | — | 100 |

EXAMPLE 31

Treatment of wounds with bioactive conjugated bandages

Burn wounds prepared on 25 guinea pigs, according to the description in materials and methods, were treated immediately after burning by bandages described in Example 29.

Each bandage was first soaked in saline solution (0.85% NaCl). The wet bandages were then placed on the burn wounds and covered by nylon, preventing thereby evaporation of water. The bandages were then replaced every 24 h.

During wounds treatment the following studies were accomplished:
A. Visual control of the cleaning of the burn wounds, including photomicrographs taken after each 24 h.
B. Measurement of wounds area cleaned from necrotic tissue after each 24 h.
C. Histological studies by biopsies taken on the 3rd, 5th and 7th days.

D. Activity of bound enzymes, before and after wounds treatment.

E. Amount of proteins adsorbed by the bandages from the wounds.

Figure 24:
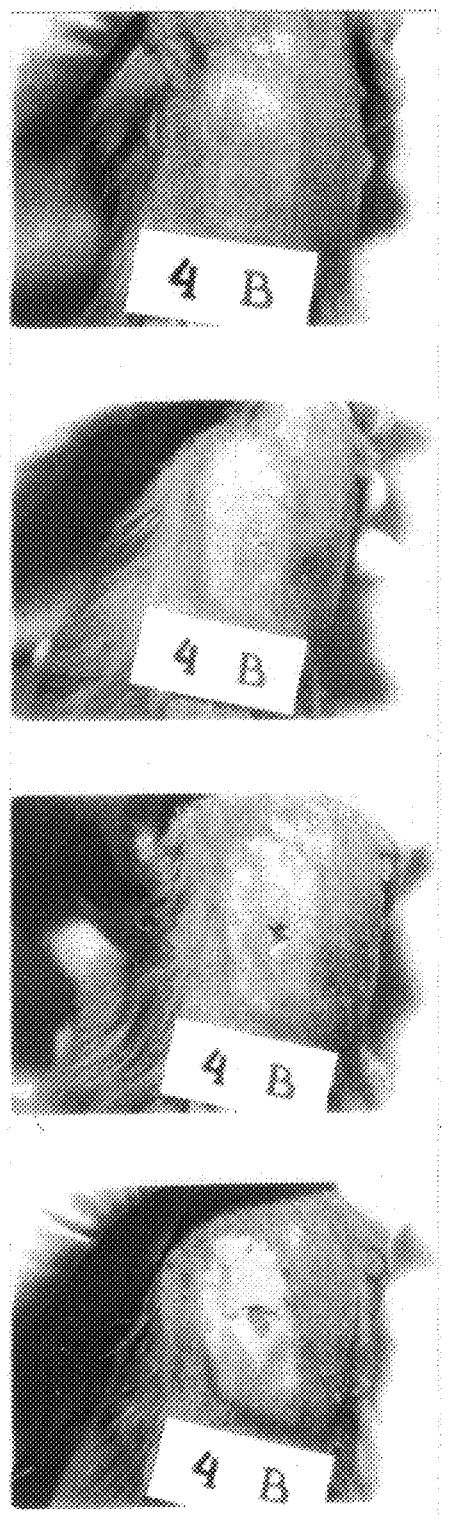
FIG. 24 compares the DALCEKS-TRYPSIN method with trypsin coupled to cellulose in accordance with an embodiment of the invention, in the treatment of burn wounds.
Figure 24:
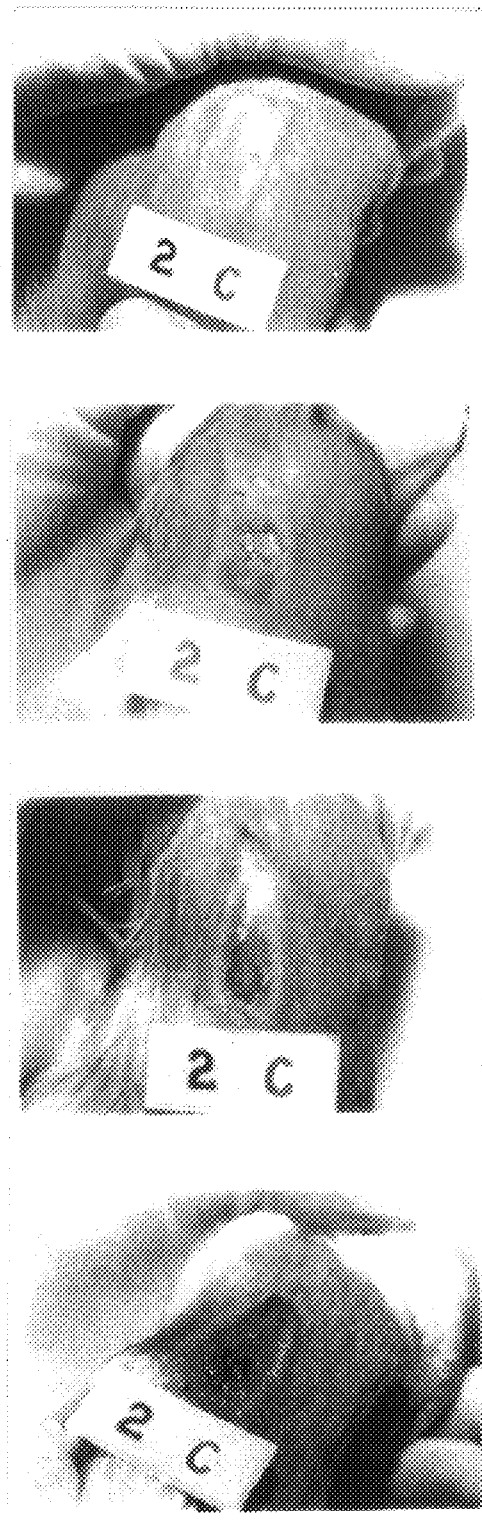

FIG. 24 and Table 12 demonstrate the significant faster cleaning of wounds from necrotic tissue treated by bandages prepared by the new activation method compared to bandages prepared by the known activation method and/or bandages composed of DALCEKS-TRYPSIN and/or PAKS-TRYPSIN.

TABLE 12

Dynamics of cleaning of burn wounds from necrotic tissue by means of bioactive conjugated bandages*

| | Area of wound, cleaned from necrotic tissue (% from all wound area) | | | |
|---|---|---|---|---|
| | Dialdehyde cellulose-trypsin | Polycapro-amide-trypsin | Cellulose-trypsin | |
| Days of treatment | (DALCEKS-TRYPSIN) | (PAKS-TRYPSIN) | Known method | Present method |
| 1 | 0 | 0–5 | 0–5 | 5–15 |
| 2 | 5–10 | 5–10 | 5–10 | 25–35 |
| 3 | 10–15 | 10–20 | 10–15 | 45–60 |
| 4 | 10–20 | 15–25 | 15–20 | 60–80 |
| 5 | 20–30 | 25–35 | 25–30 | 80–100 |
| 6 | 30–50 | 35–50 | 30–45 | 90–100 |
| 7 | 40–55 | 40–60 | 40–50 | 100 |
| 10 | 60–70 | 60–80 | 55–70 | 100 |
| 15 | 80–100 | 90–100 | 80–100 | 100 |

*Values are average of experiments carried out with 25 guinea pigs.

The results of the biopsy studies were similar to that shown in 11. Furthermore, these studies also demonstrated granulation tissue of treated for 7 days with bandages prepared by the new activation These granulation tissue are also confirmed in FIG. 24.

Figure 25:
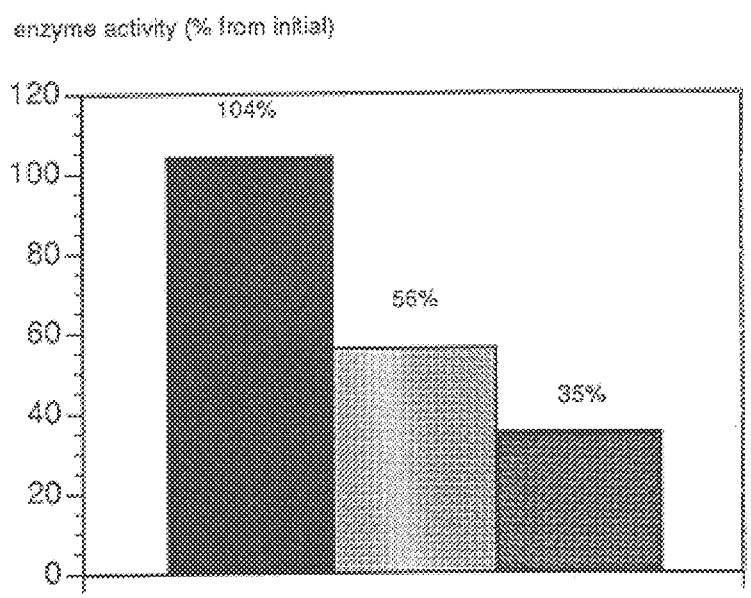
FIG. 25 depicts enzyme activity of trypsin bound polymers, after treatment of wounds.

FIG. 25 demonstrates that the enzyme activity of bandages composed DALCEKS-TRYPSIN and/or PAKS-TRYPSIN decreased by the treatment by 65% and respectively. On the other hand, the enzyme activity of bandages ed by the new and/or known activation methods did not change significantly during the wounds treatment.

The amount of proteins adsorbed from burn wounds into the bandages was studied by shaking each bandage after the wound treatment in 5 ml saline. The amount of proteins in the aqueous solution was then determined from ultraviolet spectrum at 280 nm. The largest amount of protein absorbed from burn wounds was found for bioactive conjugated bandages prepared by the new activation method (Table 13).

TABLE 13

Quantity of proteins adsorbed into bandages during wounds treatment.

| Bandage | Quantity of protein adsorbed from burn wounds (mg/bandage) |
|---|---|
| Dialdehyde cellulose-trypsin (DALCEKS-TRYPSIN) | 15.0 |
| Polycaproamide-trypsin (PAKS-TRYPSIN) | 22.6 |
| Cellulose-trypsin (Known method) | 18.3 |
| Cellulose-trypsin♦ | 42.3 |

TABLE 13-continued

Quantity of proteins adsorbed into bandages during wounds treatment.

| Bandage | Quantity of protein adsorbed from burn wounds (mg/bandage) |
|---|---|
| Cellulose-pyridine-trypsin* | 34.5 |
| Cellulose-trypsin-collagen* | 65.4 |

*cellulose pre- and post-treated with pyridine
♦present method

EXAMPLE 32

Treatment of wounds with multienzyme bandages

Figure 26:
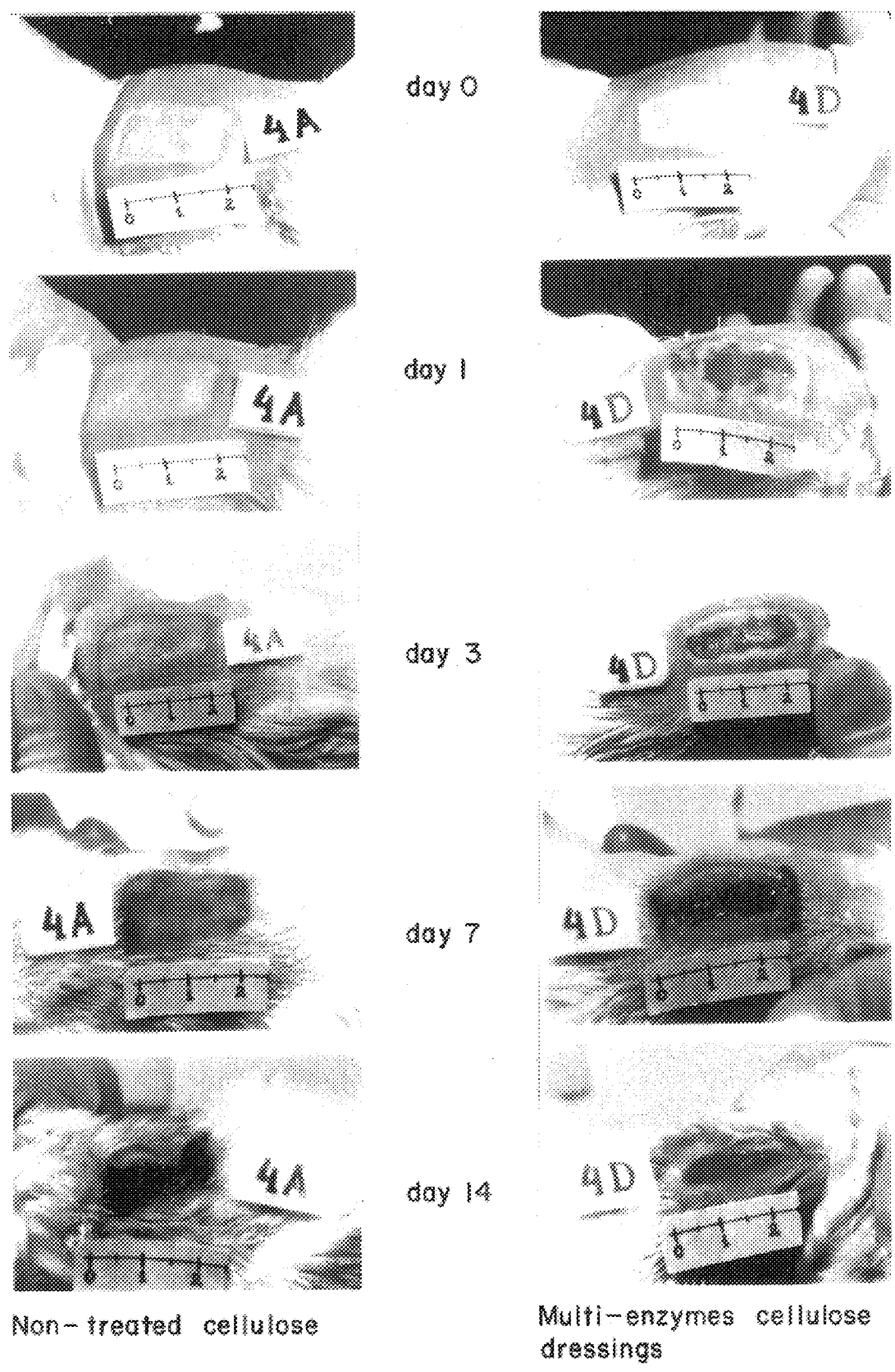
FIG. 26 compares non-treated cellulose dressings, with multienzyme cellulose dressings prepared in accordance with an embodiment of the invention.

Example 31 was repeated with non-treated cellulose and with multienzyme cellulose dressings prepared in accordance with an embodiment of the present invention, as described in Example 24. FIG. 26 shows that when using these multienzyme cellulose dressings of the present invention, the necrotic tissues exhibit a significantly faster cleaning rate, compared with non-treated cellulose dressings.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

We claim:

1. A textile web bandage, patch or like bandage, patch or like wound cover derived from a polymer composition comprising at least one member selected from the group consisting of cellulose, polysaccharides other than cellulose and polyvinyl alcohol and its copolymers which contain a plurality of free hydroxy groups, which said at least one member has been subjected to preactivation by treatment with at least one N-heterocyclic compound for a period of time sufficient to increase the capacity of said at least one member for reaction with a reactant;

said reactant being selected from the group consisting of cyanogen halides, carbonate esters, halogenated s-triazines, haloformates, sulfonyl halides and N-heterocyclic compounds containing active halogen atoms on the heterocyclic nucleus; and wherein the preactivation heterocyclic compound is selected from the group consisting of pyridine, pyrrole and pyridazine, partially hydrogenated analogs thereof, fully hydrogenated analogs thereof, and any of the foregoing which contain at least one substituent selected from $C_{1-6}$ alkyl, $C_{1-6}$ alkoxy, non-active fluorine, chlorine, bromine and trifluoromethyl.

2. The preactivated polymer of claim 1, which has been conjugated with at least one amino compound, the amino compound containing prior to conjugation at least one primary or secondary amine group.

3. The preactivated and conjugated polymer of claim 2, wherein said at least one amino compound is at least one protein.

4. The preactivated and conjugated polymer of claim 3, wherein said at least one protein is selected from trypsin, chymotrypsin, lysozyme, collagenase, albumin and hyaluronidase.

* * * * *